(12) United States Patent
Lauer et al.

(10) Patent No.: US 7,201,904 B2
(45) Date of Patent: Apr. 10, 2007

(54) EPITOPES OF HEPATITIS C VIRUS

(75) Inventors: Georg Lauer, Cambridge, MA (US);
Kei Ouchi, Cambridge, MA (US);
Bruce D. Walker, Milton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 10/440,390

(22) Filed: May 16, 2003

(65) Prior Publication Data

US 2004/0105868 A1     Jun. 3, 2004

Related U.S. Application Data

(60) Provisional application No. 60/381,273, filed on May 16, 2002.

(51) Int. Cl.
   A61K 39/00     (2006.01)
   A61K 39/12     (2006.01)
   A61K 39/29     (2006.01)
   C07K 4/02      (2006.01)
   C07K 7/00      (2006.01)

(52) U.S. Cl. .............. 424/189.1; 424/184.1; 424/186.1; 424/228.1; 530/300; 514/2

(58) Field of Classification Search .......... 424/184.1, 424/185.1, 186.1, 189.1, 204.1, 285.1, 223.1; 514/2; 530/300, 350
See application file for complete search history.

(56) References Cited

U.S. PATENT DOCUMENTS

| | | | |
|---|---|---|---|
| 5,709,995 A | 1/1998 | Chisari et al. | 435/5 |
| 2002/0115061 A1* | 8/2002 | Chisari et al. | 435/5 |
| 2003/0152580 A1* | 8/2003 | Sette et al. | 424/185.1 |
| 2004/0047877 A1* | 3/2004 | Leroux-Roels et al. | 424/185.1 |

FOREIGN PATENT DOCUMENTS

| WO | WO 93/00365 | * | 1/1993 |
|---|---|---|---|
| WO | WO 95/12677 | | 5/1995 |
| WO | WO 01/90384 | * | 11/2001 |

OTHER PUBLICATIONS

Lauer et al., Journal of Virology, vol. 76 No. 12, pp. 6104-6113 (Jun. 2002).*
Altfeld, et al., *J. Immunol.*, 167:2743-2752 (2001).
Battegay, et al., *J. Virol.*, 69(4):2462-2470 (1995).
Betts, et al., *J. Virol.*, 74(19):9144-9151 (2000).
Cerny, et al., *J. Clin. Invest.*, 95:521-530 (1995).
Chang, et al., *Hepatology*, 33(1):267-276 (2001).
Choo, et al., *Proc. Natl. Acad. Sci. USA*, 88:2451-2455 (1991).
Cooper, et al., *Immunity*, 10(4):439-449 (1999).
Dalod, et al., *J. Clin. Invest.*, 104(10):1431-1439 (1999).
Dawson, et al., *Genet. Epidemiol.*, 20(1):87-106 (2001).
Day, et al., *J. Virol.*, 75(14):6279-6291 (2001).
Giuggio, et al., *Virology*, 251(1):132-140 (1998).
Goulder, et al., *J. Exp. Med.*, 193(2):181-193 (2001).
Gruener, et al., *J. Virol.*, 75(12):5550-5558 (2001).
Grüner, et al., *J. Infect. Diseases*, 181:1528-1536 (2000).
He, et al., *Proc. Natl. Acad. Sci. USA*, 96:5692-5697 (1999).
Healey, et al., *Gastroenterology*, 110(4):A1209 (1996).
Higgins, et al., *Cabios Communications*, 5(2):151-153 (1989).
Hiroshi, et al., *Hepatology*, 25(3):705-712 (1997).
Kaneko, et al., *J. Gen. Virol.*, 77:1305-1309 (1996).
Kita, et al., *J. Gen. Virol.*, 76:3189-3193 (1995).
Kita, et al., *J. Gastroenterol.*, 30(6):809-812 (1995).
Koziel, et al., *J. Virol.*, 67(12):7522-7532 (1993).
Koziel, et al., *J. Clin. Invest.*, 96(5):2311-2321 (1995).
Koziel, et al., *J. Immunol.*, 149(10):3339-3344 (1992).
Koziel, et al., *Springer Seminars in Immunol.*, 19(1):69-83 (1997).
Kurokohchi, et al., *J. Hepatol.*, 34(6):930-935 (2001).
Kurokohchi, et al., *J. Virol.*, 70(1):232-240 (1996).
Lauer, et al., *N. Engl. J. Med.*, 345(1):41-52 (2001).
Lauer, et al., *J. Virol.*, 76(12):1-9 (2002).
Lechner, et al., *Eur. J. Immunol.*, 30(9):2479-2487 (2000).
Lechner, et al., *J. Exp. Med.*, 191(9)1499-1512 (2000).
Löhr, et al., *J. Hepatol.*, 31:407-415 (1999).
Nelson, et al., *J. Immunol.*, 158(3):1473-1481 (1997).
Rammensee, et al., *Immunogenetics*, 50(3-4):213-219 (1999).
Rehermann, et al., *J. Clin. Invest.*, 98(6):1432-1440 (1996).
Rehermann, et al., *J. Virol.*, 70(10):7092-7102 (1996).
Shirai, et al., *J. Immunol.*, 154(6):2733-2742 (1995).
Shirai, et al., *J. Virol.*, 68(5):3334-3342 (1994).
Takaki, et al., *Nat. Med.*, 6(5):578-582 (2000).
Thimme, et al., *J. Exp. Med.*, 194(10):1395-1406 (2001).
Urbani, et al., *Hepatology*, 33(6):1533-1543 (2001).
Wedemeyer, et al., *J. Virol.*, 75(23):11392-11400 (2001).
Wong, et al., *J. Virol.*, 75(3):1229-1235 (2001).
Wong, et al., *J. Immunol.*, 160:1479-1488 (1998).
International Search Report for PCT/US03/15443, mailed Oct. 31, 2005.

* cited by examiner

*Primary Examiner*—Bruce R. Campell
*Assistant Examiner*—Zachariah Lucas
(74) *Attorney, Agent, or Firm*—Mintz, Levin, Cohn, Ferris, Glovsky and Popeo, P.C.; Ingrid A. Beattie

(57) ABSTRACT

The invention provides compositions containing HCV epitopes, which are recognized by cytotoxic T lymphocytes. Such polypeptides are used in prophylactic vaccines, immunotherapies, and assays to monitor the progress or success of immune interventions. The compositions are optimized to elicit an immune response in a genetically-diverse population of individuals.

2 Claims, 19 Drawing Sheets

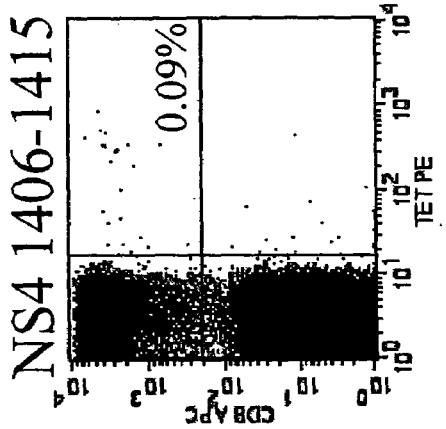
Fig. 1D NS4 1406-1415
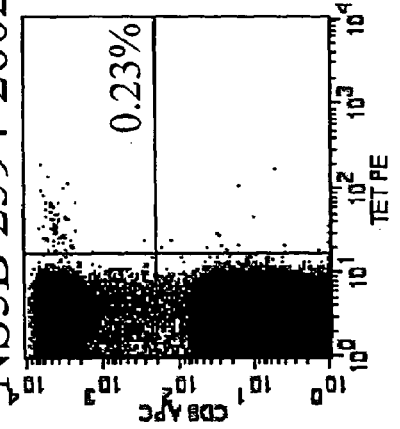
Fig. 1G NS5B 2594-2602
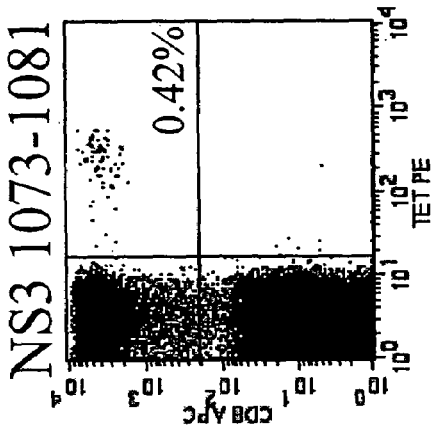
Fig. 1C NS3 1073-1081
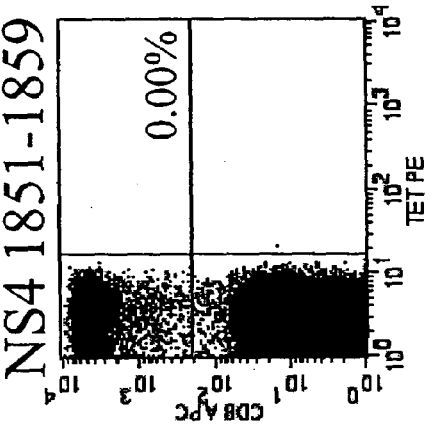
Fig. 1F NS4 1851-1859
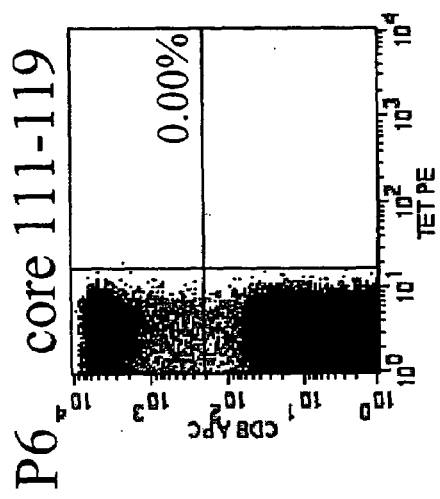
Fig. 1B P6 core 111-119
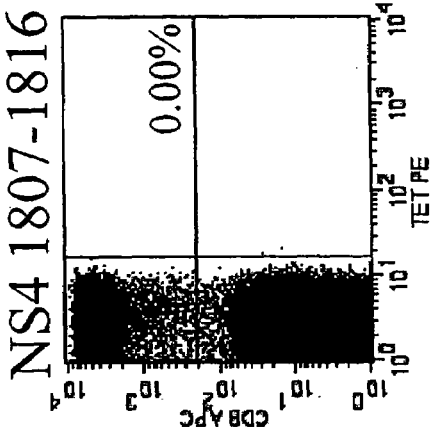
Fig. 1E NS4 1807-1816

No peptide

P951-970

P0

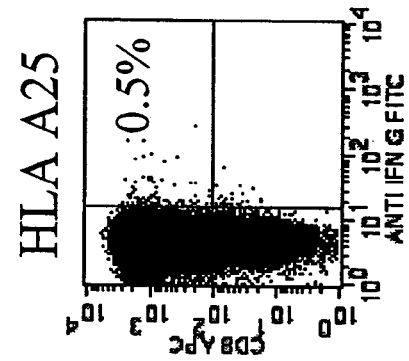
Fig. 3E HLA A25
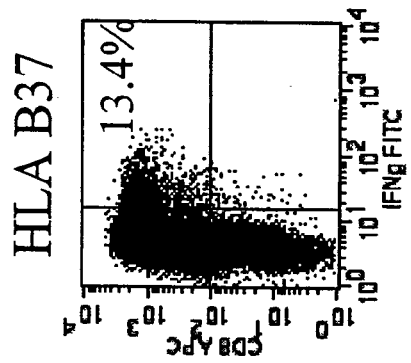
Fig. 3D HLA B37
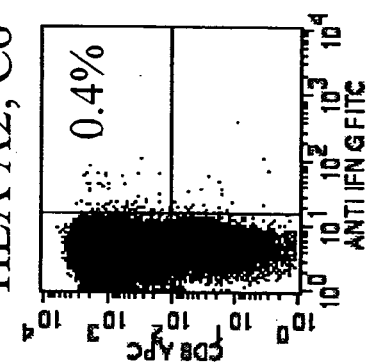
Fig. 3G HLA A2, C6
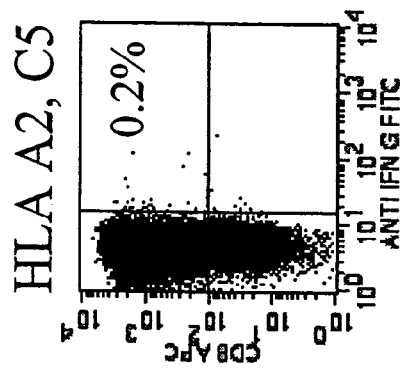
Fig. 3C HLA A2, C5
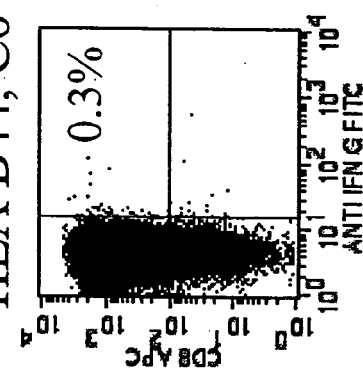
Fig. 3F HLA B44, C6

Fig. 3H

RDWAHNGLR Seq ID No.:98
RDWAHNGL Seq ID No.:32
LRDWAHNGL Seq ID No.:99
PLRDWAHNGLRD Seq ID No.:100

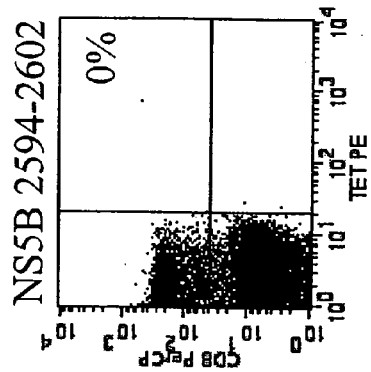
Fig. 5A P14 Direct ex-vivo — NS3 1073-1081 — 0.17%
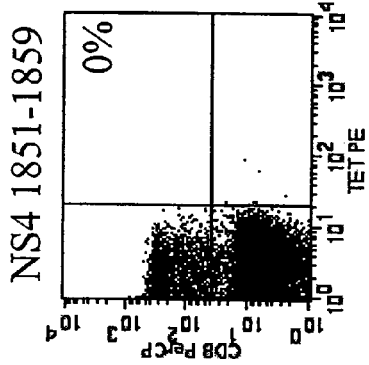
Fig. 5B NS4 1406-1415 — 0%
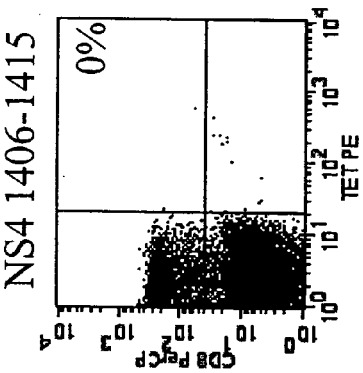
Fig. 5C NS4 1851-1859 — 0%
Fig. 5D NS5B 2594-2602 — 0%
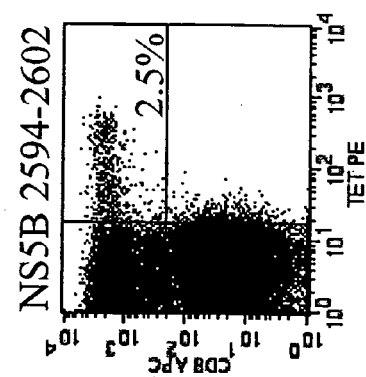
Fig. 5E P14 After peptide stimulation (9d) — NS3 1073-1081 — 31%
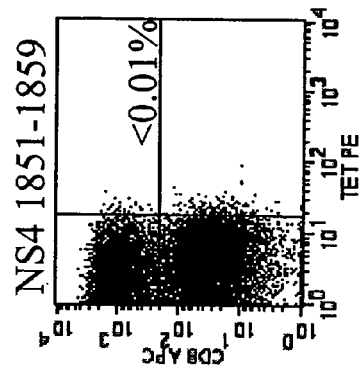
Fig. 5F NS4 1406-1415 — 6.6%
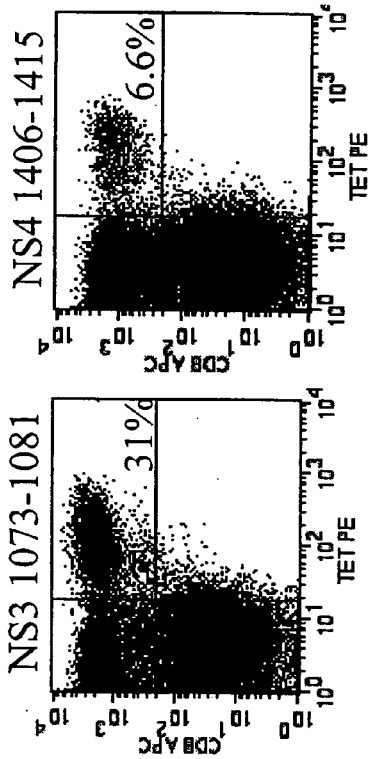
Fig. 5G NS4 1851-1859 — <0.01%
Fig. 5H NS5B 2594-2602 — 2.5%

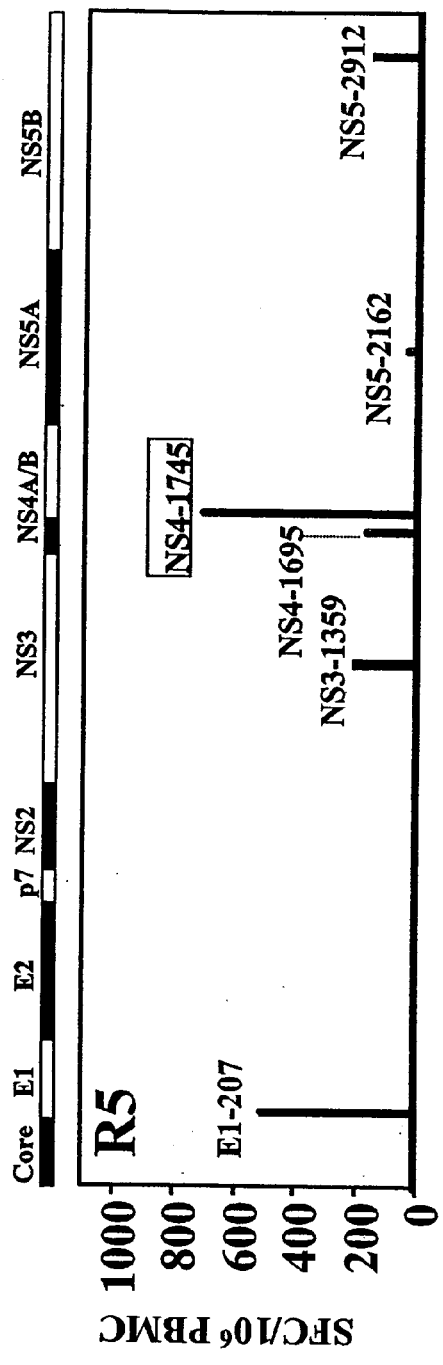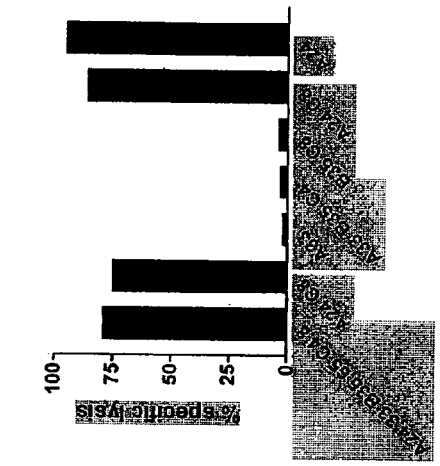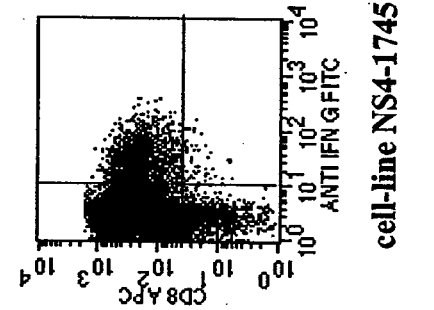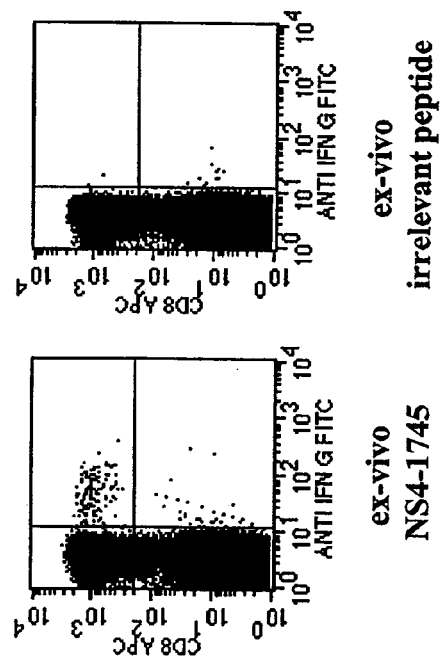
Fig. 6A
Fig. 6B
Fig. 6C ex-vivo irrelevant peptide
Fig. 6D cell-line NS4-1745
Fig. 6E

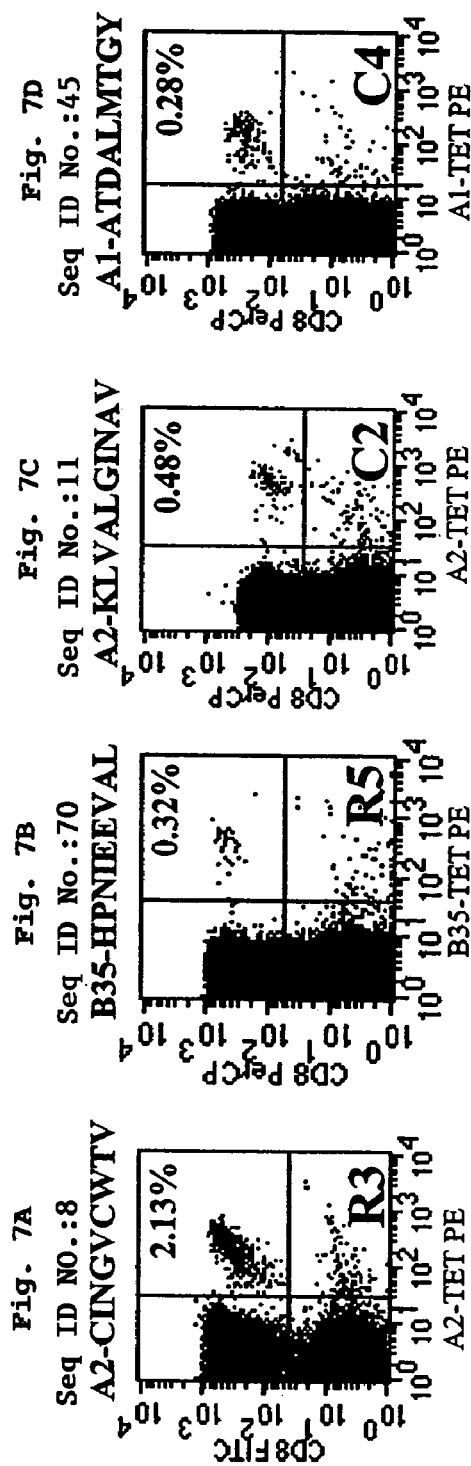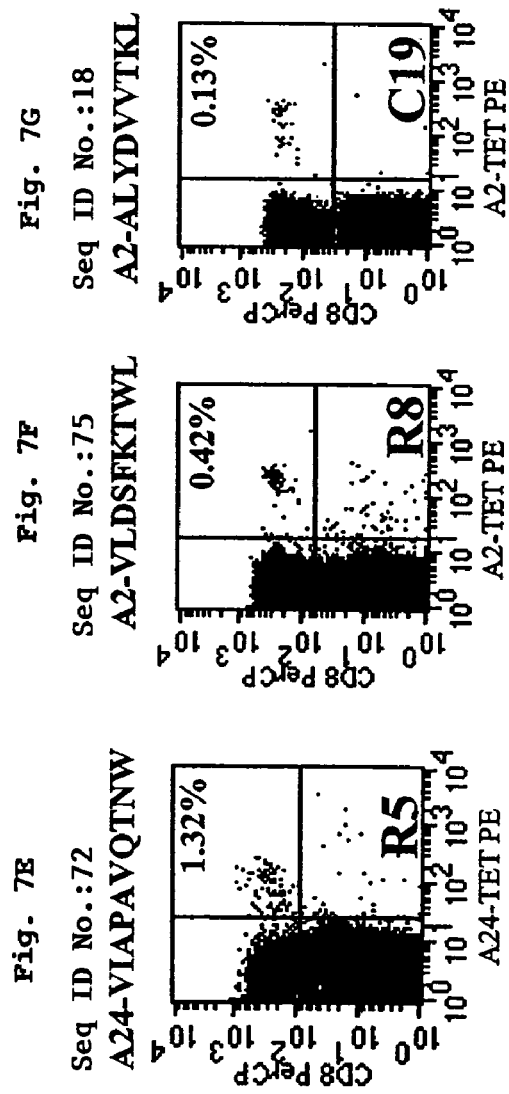

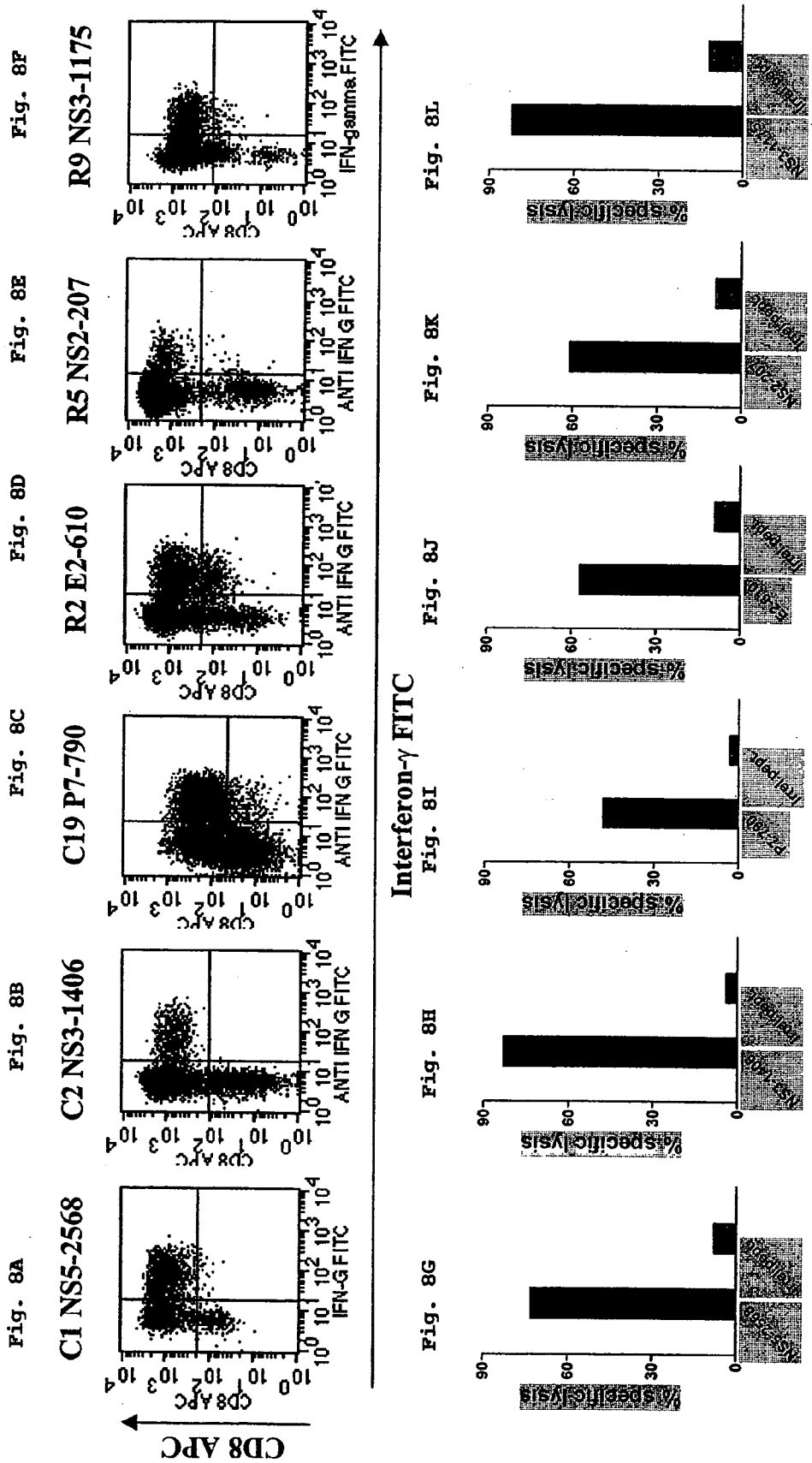

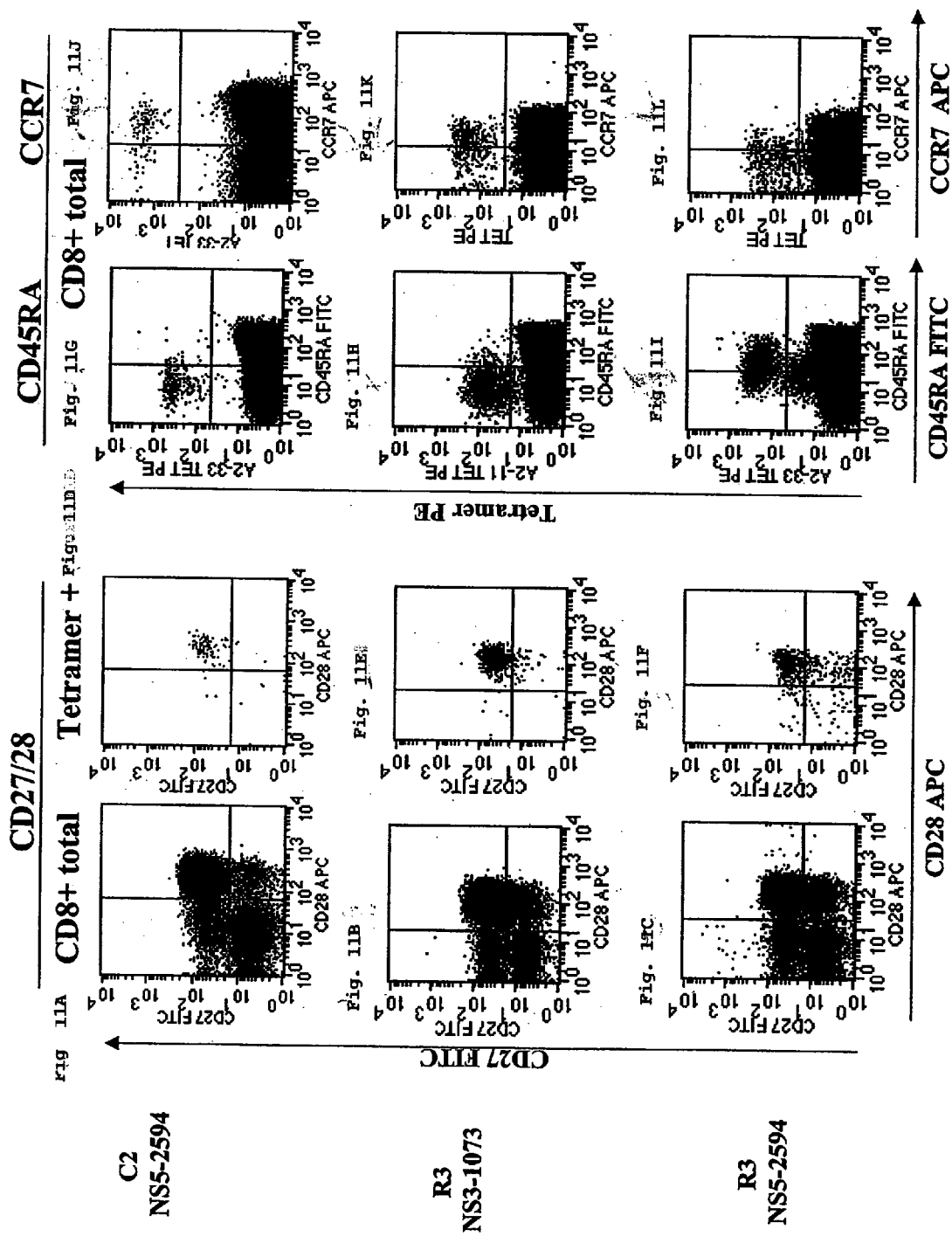

```
                       SEQUENCE LISTING

<160> NUMBER OF SEQ ID NOS: 100

<210> SEQ ID NO 1
<211> LENGTH: 10
<212> TYPE: PRT
<213> ORGANISM: Hepatitis C virus

<400> SEQUENCE: 1

Tyr Leu Leu Pro Arg Arg Gly Pro Arg Leu
  1               5                  10

<210> SEQ ID NO 2
<211> LENGTH: 9
<212> TYPE: PRT
<213> ORGANISM: Hepatitis C virus

<400> SEQUENCE: 2

Asp Leu Met Gly Tyr Ile Pro Leu Val
  1               5

<210> SEQ ID NO 3
<211> LENGTH: 10
<212> TYPE: PRT
<213> ORGANISM: Hepatitis C virus

<400> SEQUENCE: 3

Leu Leu Ala Leu Leu Ser Cys Leu Thr Val
  1               5                  10

<210> SEQ ID NO 4
<211> LENGTH: 8
<212> TYPE: PRT
<213> ORGANISM: Hepatitis C virus

<400> SEQUENCE: 4
```

```
Ile Leu His Thr Pro Gly Cys Val
  1               5

<210> SEQ ID NO 5
<211> LENGTH: 10
<212> TYPE: PRT
<213> ORGANISM: Hepatitis C virus

<400> SEQUENCE: 5

Gln Leu Arg Arg His Ile Asp Leu Leu Val
  1               5                  10

<210> SEQ ID NO 6
<211> LENGTH: 9
<212> TYPE: PRT
<213> ORGANISM: Hepatitis C virus

<400> SEQUENCE: 6

Ser Met Val Gly Asn Trp Ala Lys Val
  1               5

<210> SEQ ID NO 7
<211> LENGTH: 11
<212> TYPE: PRT
<213> ORGANISM: Hepatitis C virus

<400> SEQUENCE: 7

Ser Leu Leu Ala Pro Gly Ala Lys Gln Asn Val
  1               5                  10

<210> SEQ ID NO 8
<211> LENGTH: 9
<212> TYPE: PRT
<213> ORGANISM: Hepatitis C virus

<400> SEQUENCE: 8

Cys Ile Asn Gly Val Cys Trp Thr Val
  1               5

<210> SEQ ID NO 9
<211> LENGTH: 9
<212> TYPE: PRT
<213> ORGANISM: Hepatitis C virus

<400> SEQUENCE: 9

Leu Leu Cys Pro Ala Gly His Ala Val
  1               5

<210> SEQ ID NO 10
<211> LENGTH: 10
<212> TYPE: PRT
<213> ORGANISM: Hepatitis C virus

<400> SEQUENCE: 10

Thr Gly Ala Pro Val Thr Tyr Ser Thr Tyr
  1               5                  10

<210> SEQ ID NO 11
<211> LENGTH: 10
<212> TYPE: PRT
<213> ORGANISM: Hepatitis C virus

<400> SEQUENCE: 11

Lys Leu Val Ala Leu Gly Ile Asn Ala Val
```

-continued

```
              1               5                  10
```

```
<210> SEQ ID NO 12
<211> LENGTH: 9
<212> TYPE: PRT
<213> ORGANISM: Hepatitis C virus

<400> SEQUENCE: 12

Ser Leu Met Ala Phe Thr Ala Ala Val
 1               5

<210> SEQ ID NO 13
<211> LENGTH: 10
<212> TYPE: PRT
<213> ORGANISM: Hepatitis C virus

<400> SEQUENCE: 13

Leu Leu Phe Asn Ile Leu Gly Gly Trp Val
 1               5                  10

<210> SEQ ID NO 14
<211> LENGTH: 9
<212> TYPE: PRT
<213> ORGANISM: Hepatitis C virus

<400> SEQUENCE: 14

Ile Leu Ala Gly Tyr Gly Ala Gly Val
 1               5

<210> SEQ ID NO 15
<211> LENGTH: 11
<212> TYPE: PRT
<213> ORGANISM: Hepatitis C virus

<400> SEQUENCE: 15

Ser Pro Asp Ala Glu Leu Ile Glu Ala Asn Leu
 1               5                  10

<210> SEQ ID NO 16
<211> LENGTH: 9
<212> TYPE: PRT
<213> ORGANISM: Hepatitis C virus

<400> SEQUENCE: 16

Ile Leu Asp Ser Phe Asp Pro Leu Val
 1               5

<210> SEQ ID NO 17
<211> LENGTH: 9
<212> TYPE: PRT
<213> ORGANISM: Hepatitis C virus

<400> SEQUENCE: 17

Ala Leu Tyr Asp Val Val Thr Lys Leu
 1               5

<210> SEQ ID NO 18
<211> LENGTH: 10
<212> TYPE: PRT
<213> ORGANISM: Hepatitis C virus

<400> SEQUENCE: 18

Arg Leu Ile Val Phe Pro Asp Leu Gly Val
 1               5                  10
```

```
<210> SEQ ID NO 19
<211> LENGTH: 9
<212> TYPE: PRT
<213> ORGANISM: Hepatitis C virus

<400> SEQUENCE: 19

Gly Leu Gln Asp Cys Thr Met Leu Val
 1               5

<210> SEQ ID NO 20
<211> LENGTH: 9
<212> TYPE: PRT
<213> ORGANISM: Hepatitis C virus

<400> SEQUENCE: 20

Ser Leu Thr Pro Pro His Ser Ala Lys
 1               5

<210> SEQ ID NO 21
<211> LENGTH: 9
<212> TYPE: PRT
<213> ORGANISM: Hepatitis C virus

<400> SEQUENCE: 21

Arg Val Cys Glu Lys Met Ala Leu Tyr
 1               5

<210> SEQ ID NO 22
<211> LENGTH: 9
<212> TYPE: PRT
<213> ORGANISM: Hepatitis C virus

<400> SEQUENCE: 22

Met Ser Thr Asn Pro Lys Pro Gln Lys
 1               5

<210> SEQ ID NO 23
<211> LENGTH: 8
<212> TYPE: PRT
<213> ORGANISM: Hepatitis C virus

<400> SEQUENCE: 23

Thr Ile Asn Tyr Thr Ile Phe Lys
 1               5

<210> SEQ ID NO 24
<211> LENGTH: 10
<212> TYPE: PRT
<213> ORGANISM: Hepatitis C virus

<400> SEQUENCE: 24

Thr Leu Gly Phe Gly Ala Tyr Met Ser Lys
 1               5                  10

<210> SEQ ID NO 25
<211> LENGTH: 8
<212> TYPE: PRT
<213> ORGANISM: Hepatitis C virus

<400> SEQUENCE: 25

Thr Leu Thr His Pro Val Thr Lys
 1               5

<210> SEQ ID NO 26
```

-continued

```
<211> LENGTH: 9
<212> TYPE: PRT
<213> ORGANISM: Hepatitis C virus

<400> SEQUENCE: 26

Ala Tyr Ser Gln Gln Thr Arg Gly Leu
 1               5

<210> SEQ ID NO 27
<211> LENGTH: 8
<212> TYPE: PRT
<213> ORGANISM: Hepatitis C virus

<400> SEQUENCE: 27

Met Ala Leu Thr Leu Ser Pro Tyr
 1               5

<210> SEQ ID NO 28
<211> LENGTH: 9
<212> TYPE: PRT
<213> ORGANISM: Hepatitis C virus

<400> SEQUENCE: 28

Gly Pro Arg Leu Gly Val Arg Ala Thr
 1               5

<210> SEQ ID NO 29
<211> LENGTH: 9
<212> TYPE: PRT
<213> ORGANISM: Hepatitis C virus

<400> SEQUENCE: 29

Asp Pro Arg Arg Arg Ser Arg Asn Leu
 1               5

<210> SEQ ID NO 30
<211> LENGTH: 9
<212> TYPE: PRT
<213> ORGANISM: Hepatitis C virus

<400> SEQUENCE: 30

His Ser Lys Lys Lys Cys Asp Glu Leu
 1               5

<210> SEQ ID NO 31
<211> LENGTH: 8
<212> TYPE: PRT
<213> ORGANISM: Hepatitis C virus

<400> SEQUENCE: 31

Leu Ile Arg Leu Lys Pro Thr Leu
 1               5

<210> SEQ ID NO 32
<211> LENGTH: 8
<212> TYPE: PRT
<213> ORGANISM: Hepatitis C virus

<400> SEQUENCE: 32

Arg Asp Trp Ala His Asn Gly Leu
 1               5

<210> SEQ ID NO 33
<211> LENGTH: 11
<212> TYPE: PRT
```

-continued

<213> ORGANISM: Hepatitis C virus

<400> SEQUENCE: 33

Ser Glu Cys Thr Thr Pro Cys Ser Gly Ser Trp
 1               5                  10

<210> SEQ ID NO 34
<211> LENGTH: 9
<212> TYPE: PRT
<213> ORGANISM: Hepatitis C virus

<400> SEQUENCE: 34

Asn Glu Gly Cys Gly Trp Ala Gly Trp
 1               5

<210> SEQ ID NO 35
<211> LENGTH: 10
<212> TYPE: PRT
<213> ORGANISM: Hepatitis C virus

<400> SEQUENCE: 35

Cys Val Ile Gly Gly Ala Gly Asn Asn Thr
 1               5                  10

<210> SEQ ID NO 36
<211> LENGTH: 9
<212> TYPE: PRT
<213> ORGANISM: Hepatitis C virus

<400> SEQUENCE: 36

Lys Ser Lys Lys Thr Pro Met Gly Phe
 1               5

<210> SEQ ID NO 37
<211> LENGTH: 10
<212> TYPE: PRT
<213> ORGANISM: Hepatitis C virus

<400> SEQUENCE: 37

Gly Gln Ile Val Gly Gly Val Tyr Leu Leu
 1               5                  10

<210> SEQ ID NO 38
<211> LENGTH: 10
<212> TYPE: PRT
<213> ORGANISM: Hepatitis C virus

<400> SEQUENCE: 38

Gly Glu Asn Asp Thr Asp Val Phe Val Leu
 1               5                  10

<210> SEQ ID NO 39
<211> LENGTH: 9
<212> TYPE: PRT
<213> ORGANISM: Hepatitis C virus

<400> SEQUENCE: 39

Leu Glu Asp Arg Asp Arg Ser Glu Leu
 1               5

<210> SEQ ID NO 40
<211> LENGTH: 9
<212> TYPE: PRT
<213> ORGANISM: Hepatitis C virus

```
<400> SEQUENCE: 40

His Glu Tyr Pro Val Gly Ser Gln Leu
 1               5

<210> SEQ ID NO 41
<211> LENGTH: 10
<212> TYPE: PRT
<213> ORGANISM: Hepatitis C virus

<400> SEQUENCE: 41

Arg Glu Ile Ser Val Pro Ala Glu Ile Leu
 1               5                  10

<210> SEQ ID NO 42
<211> LENGTH: 9
<212> TYPE: PRT
<213> ORGANISM: Hepatitis C virus

<400> SEQUENCE: 42

Asp Tyr Pro Tyr Arg Leu Trp His Tyr
 1               5

<210> SEQ ID NO 43
<211> LENGTH: 20
<212> TYPE: PRT
<213> ORGANISM: Hepatitis C virus

<400> SEQUENCE: 43

Lys Trp Val Pro Gly Ala Val Tyr Thr Phe Tyr Gly Met Trp Pro Leu
 1               5                  10                  15

Leu Leu Leu Leu
            20

<210> SEQ ID NO 44
<211> LENGTH: 20
<212> TYPE: PRT
<213> ORGANISM: Hepatitis C virus

<400> SEQUENCE: 44

Cys Pro Ala Gly His Ala Val Gly Ile Phe Arg Ala Ala Val Cys Thr
 1               5                  10                  15

Arg Gly Val Ala
            20

<210> SEQ ID NO 45
<211> LENGTH: 9
<212> TYPE: PRT
<213> ORGANISM: Hepatitis C virus

<400> SEQUENCE: 45

Ala Thr Asp Ala Leu Met Thr Gly Tyr
 1               5

<210> SEQ ID NO 46
<211> LENGTH: 20
<212> TYPE: PRT
<213> ORGANISM: Hepatitis C virus

<400> SEQUENCE: 46

Ala Arg Gly Ser Pro Pro Ser Val Ala Ser Ser Ser Ala Ser Gln Leu
 1               5                  10                  15

Ser Ala Pro Ser
            20
```

```
<210> SEQ ID NO 47
<211> LENGTH: 10
<212> TYPE: PRT
<213> ORGANISM: Hepatitis C virus

<400> SEQUENCE: 47

Gln Pro Glu Lys Gly Gly Arg Lys Pro Ala
 1               5                  10

<210> SEQ ID NO 48
<211> LENGTH: 10
<212> TYPE: PRT
<213> ORGANISM: Hepatitis C virus

<400> SEQUENCE: 48

Ser Pro Gly Glu Ile Asn Arg Val Ala Ala
 1               5                  10

<210> SEQ ID NO 49
<211> LENGTH: 8
<212> TYPE: PRT
<213> ORGANISM: Hepatitis C virus

<400> SEQUENCE: 49

Cys Pro Asn Ser Ser Ile Val Tyr
 1               5

<210> SEQ ID NO 50
<211> LENGTH: 10
<212> TYPE: PRT
<213> ORGANISM: Hepatitis C virus

<400> SEQUENCE: 50

Asn Thr Arg Pro Pro Leu Gly Asn Trp Phe
 1               5                  10

<210> SEQ ID NO 51
<211> LENGTH: 9
<212> TYPE: PRT
<213> ORGANISM: Hepatitis C virus

<400> SEQUENCE: 51

Phe Tyr Gly Met Trp Pro Leu Leu Leu
 1               5

<210> SEQ ID NO 52
<211> LENGTH: 8
<212> TYPE: PRT
<213> ORGANISM: Hepatitis C virus

<400> SEQUENCE: 52

Phe Tyr Gly Met Trp Pro Leu Leu
 1               5

<210> SEQ ID NO 53
<211> LENGTH: 9
<212> TYPE: PRT
<213> ORGANISM: Hepatitis C virus

<400> SEQUENCE: 53

His Ala Val Gly Leu Phe Arg Ala Ala
 1               5
```

```
<210> SEQ ID NO 54
<211> LENGTH: 9
<212> TYPE: PRT
<213> ORGANISM: Hepatitis C virus

<400> SEQUENCE: 54

Leu Thr Thr Ser Gln Thr Leu Leu Phe
 1               5

<210> SEQ ID NO 55
<211> LENGTH: 8
<212> TYPE: PRT
<213> ORGANISM: Hepatitis C virus

<400> SEQUENCE: 55

Ile Pro Asp Arg Glu Val Leu Tyr
 1               5

<210> SEQ ID NO 56
<211> LENGTH: 10
<212> TYPE: PRT
<213> ORGANISM: Hepatitis C virus

<400> SEQUENCE: 56

Val Ile Ala Pro Ala Val Gln Thr Asn Trp
 1               5                  10

<210> SEQ ID NO 57
<211> LENGTH: 9
<212> TYPE: PRT
<213> ORGANISM: Hepatitis C virus

<400> SEQUENCE: 57

Glu Pro Glu Pro Asp Val Ala Val Leu
 1               5

<210> SEQ ID NO 58
<211> LENGTH: 10
<212> TYPE: PRT
<213> ORGANISM: Hepatitis C virus

<400> SEQUENCE: 58

Leu Gly Val Pro Pro Leu Arg Ala Trp Arg
 1               5                  10

<210> SEQ ID NO 59
<211> LENGTH: 10
<212> TYPE: PRT
<213> ORGANISM: Hepatitis C virus

<400> SEQUENCE: 59

Tyr Arg Leu Trp His Tyr Pro Cys Thr Ile
 1               5                  10

<210> SEQ ID NO 60
<211> LENGTH: 20
<212> TYPE: PRT
<213> ORGANISM: Hepatitis C virus

<400> SEQUENCE: 60

Ala Thr Cys Ile Asn Gly Val Cys Trp Thr Val Tyr His Gly Ala Gly
 1               5                  10                  15

Thr Arg Thr Ile
            20
```

```
<210> SEQ ID NO 61
<211> LENGTH: 10
<212> TYPE: PRT
<213> ORGANISM: Hepatitis C virus

<400> SEQUENCE: 61

Tyr Arg Leu Trp His Tyr Pro Cys Thr Ile
 1               5                  10

<210> SEQ ID NO 62
<211> LENGTH: 10
<212> TYPE: PRT
<213> ORGANISM: Hepatitis C virus

<400> SEQUENCE: 62

Leu Ser Pro Tyr Tyr Lys Arg Tyr Ile Ser
 1               5                  10

<210> SEQ ID NO 63
<211> LENGTH: 9
<212> TYPE: PRT
<213> ORGANISM: Hepatitis C virus

<400> SEQUENCE: 63

Cys Ile Asn Gly Val Cys Trp Thr Val
 1               5

<210> SEQ ID NO 64
<211> LENGTH: 9
<212> TYPE: PRT
<213> ORGANISM: Hepatitis C virus

<400> SEQUENCE: 64

Glu Thr Phe Trp Ala Lys His Met Trp
 1               5

<210> SEQ ID NO 65
<211> LENGTH: 11
<212> TYPE: PRT
<213> ORGANISM: Hepatitis C virus

<400> SEQUENCE: 65

Ser Glu Cys Cys Thr Pro Cys Ser Gly Ser Trp
 1               5                  10

<210> SEQ ID NO 66
<211> LENGTH: 9
<212> TYPE: PRT
<213> ORGANISM: Hepatitis C virus

<400> SEQUENCE: 66

Glu Leu Ile Glu Ala Asn Leu Leu Trp
 1               5

<210> SEQ ID NO 67
<211> LENGTH: 10
<212> TYPE: PRT
<213> ORGANISM: Hepatitis C virus

<400> SEQUENCE: 67

Thr Ala Arg His Thr Pro Val Asn Ser Trp
 1               5                  10

<210> SEQ ID NO 68
```

-continued

```
<211> LENGTH: 9
<212> TYPE: PRT
<213> ORGANISM: Hepatitis C virus

<400> SEQUENCE: 68

Asn Glu Gly Cys Gly Trp Met Gly Trp
 1               5

<210> SEQ ID NO 69
<211> LENGTH: 8
<212> TYPE: PRT
<213> ORGANISM: Hepatitis C virus

<400> SEQUENCE: 69

Cys Pro Asn Ser Ser Ile Val Tyr
 1               5

<210> SEQ ID NO 70
<211> LENGTH: 9
<212> TYPE: PRT
<213> ORGANISM: Hepatitis C virus

<400> SEQUENCE: 70

His Pro Asn Ile Glu Glu Val Ala Leu
 1               5

<210> SEQ ID NO 71
<211> LENGTH: 8
<212> TYPE: PRT
<213> ORGANISM: Hepatitis C virus

<400> SEQUENCE: 71

Ile Pro Asp Arg Glu Val Leu Tyr
 1               5

<210> SEQ ID NO 72
<211> LENGTH: 10
<212> TYPE: PRT
<213> ORGANISM: Hepatitis C virus

<400> SEQUENCE: 72

Val Ile Ala Pro Ala Val Gln Thr Asn Trp
 1               5                  10

<210> SEQ ID NO 73
<211> LENGTH: 9
<212> TYPE: PRT
<213> ORGANISM: Hepatitis C virus

<400> SEQUENCE: 73

Glu Pro Glu Pro Asp Val Ala Val Leu
 1               5

<210> SEQ ID NO 74
<211> LENGTH: 10
<212> TYPE: PRT
<213> ORGANISM: Hepatitis C virus

<400> SEQUENCE: 74

Leu Gly Val Pro Pro Leu Arg Ala Trp Arg
 1               5                  10

<210> SEQ ID NO 75
<211> LENGTH: 9
<212> TYPE: PRT
```

-continued

<213> ORGANISM: Hepatitis C virus

<400> SEQUENCE: 75

Val Leu Asp Ser Phe Lys Thr Trp Leu
 1               5

<210> SEQ ID NO 76
<211> LENGTH: 20
<212> TYPE: PRT
<213> ORGANISM: Hepatitis C virus

<400> SEQUENCE: 76

Thr Ser Arg Ser Ala Cys Gln Arg Gln Lys Lys Val Thr Phe Asp Arg
 1               5                  10                  15

Leu Gln Val Leu
            20

<210> SEQ ID NO 77
<211> LENGTH: 11
<212> TYPE: PRT
<213> ORGANISM: Hepatitis C virus

<400> SEQUENCE: 77

Asn Thr Arg Pro Pro Leu Gly Asn Trp Phe Gly
 1               5                  10

<210> SEQ ID NO 78
<211> LENGTH: 9
<212> TYPE: PRT
<213> ORGANISM: Hepatitis C virus

<400> SEQUENCE: 78

His Ala Val Gly Leu Phe Arg Ala Ala
 1               5

<210> SEQ ID NO 79
<211> LENGTH: 10
<212> TYPE: PRT
<213> ORGANISM: Hepatitis C virus

<400> SEQUENCE: 79

Leu Gly Val Pro Pro Leu Arg Ala Trp Arg
 1               5                  10

<210> SEQ ID NO 80
<211> LENGTH: 9
<212> TYPE: PRT
<213> ORGANISM: Hepatitis C virus

<400> SEQUENCE: 80

Leu Thr Thr Ser Gln Thr Leu Leu Phe
 1               5

<210> SEQ ID NO 81
<211> LENGTH: 10
<212> TYPE: PRT
<213> ORGANISM: Hepatitis C virus

<400> SEQUENCE: 81

Leu Gly Val Pro Pro Leu Arg Ala Trp Arg
 1               5                  10

<210> SEQ ID NO 82
<211> LENGTH: 11

```
<212> TYPE: PRT
<213> ORGANISM: Hepatitis C virus

<400> SEQUENCE: 82

Asn Thr Arg Pro Pro Leu Gly Asn Trp Phe Gly
  1               5                  10

<210> SEQ ID NO 83
<211> LENGTH: 20
<212> TYPE: PRT
<213> ORGANISM: Hepatitis C virus

<400> SEQUENCE: 83

Leu Gly Ala Leu Thr Gly Thr Tyr Val Tyr Asn His Leu Thr Pro Leu
  1               5                  10                  15

Arg Asp Trp Ala
             20

<210> SEQ ID NO 84
<211> LENGTH: 20
<212> TYPE: PRT
<213> ORGANISM: Hepatitis C virus

<400> SEQUENCE: 84

Val Phe Thr Gly Leu Thr His Ile Asp Ala His Phe Leu Ser Gln Thr
  1               5                  10                  15

Lys Gln Ser Gly
             20

<210> SEQ ID NO 85
<211> LENGTH: 20
<212> TYPE: PRT
<213> ORGANISM: Hepatitis C virus

<400> SEQUENCE: 85

Gly Ile Gln Tyr Leu Ala Gly Leu Ser Thr Leu Pro Gly Asn Pro Ala
  1               5                  10                  15

Ile Ala Ser Leu
             20

<210> SEQ ID NO 86
<211> LENGTH: 20
<212> TYPE: PRT
<213> ORGANISM: Hepatitis C virus

<400> SEQUENCE: 86

Leu Thr Thr Ser Gln Thr Leu Leu Phe Asn Ile Leu Gly Gly Trp Val
  1               5                  10                  15

Ala Ala Gln Leu
             20

<210> SEQ ID NO 87
<211> LENGTH: 18
<212> TYPE: PRT
<213> ORGANISM: Hepatitis C virus

<400> SEQUENCE: 87

Cys Leu Ile Arg Leu Lys Pro Thr Leu His Gly Pro Thr Pro Leu Leu
  1               5                  10                  15

Tyr Arg

<210> SEQ ID NO 88
```

-continued

<211> LENGTH: 9
<212> TYPE: PRT
<213> ORGANISM: Hepatitis C virus

<400> SEQUENCE: 88

Met Met Met Asn Trp Ser Pro Thr Thr
1 5

<210> SEQ ID NO 89
<211> LENGTH: 8
<212> TYPE: PRT
<213> ORGANISM: Hepatitis C virus

<400> SEQUENCE: 89

Phe Tyr Gly Met Trp Pro Leu Leu
1 5

<210> SEQ ID NO 90
<211> LENGTH: 21
<212> TYPE: PRT
<213> ORGANISM: Hepatitis C virus

<400> SEQUENCE: 90

His Cys Pro Ala Gly His Ala Val Gly Ile Phe Arg Ala Ala Val Cys
1 5 10 15

Thr Arg Gly Val Ala
20

<210> SEQ ID NO 91
<211> LENGTH: 20
<212> TYPE: PRT
<213> ORGANISM: Hepatitis C virus

<400> SEQUENCE: 91

Leu Ser Pro Tyr Tyr Lys Arg Tyr Ile Ser Trp Cys Leu Trp Trp Leu
1 5 10 15

Gln Tyr Phe Leu
20

<210> SEQ ID NO 92
<211> LENGTH: 20
<212> TYPE: PRT
<213> ORGANISM: Hepatitis C virus

<400> SEQUENCE: 92

Asp Ala Val Ile Leu Leu Met Cys Ala Val His Pro Thr Leu Val Phe
1 5 10 15

Asp Ile Thr Lys
20

<210> SEQ ID NO 93
<211> LENGTH: 10
<212> TYPE: PRT
<213> ORGANISM: Hepatitis C virus

<400> SEQUENCE: 93

Tyr Arg Leu Trp His Tyr Pro Cys Thr Ile
1 5 10

<210> SEQ ID NO 94
<211> LENGTH: 11
<212> TYPE: PRT
<213> ORGANISM: Hepatitis C virus

```
-continued

<400> SEQUENCE: 94

Glu Val Ile Ala Pro Ala Val Gln Thr Asn Trp
1               5                   10

<210> SEQ ID NO 95
<211> LENGTH: 8
<212> TYPE: PRT
<213> ORGANISM: Hepatitis C virus

<400> SEQUENCE: 95

Ala Ala Arg Val Thr Ala Ile Leu
1               5

<210> SEQ ID NO 96
<211> LENGTH: 9
<212> TYPE: PRT
<213> ORGANISM: Hepatitis C virus

<400> SEQUENCE: 96

Phe Tyr Gly Met Trp Pro Leu Leu Leu
1               5

<210> SEQ ID NO 97
<211> LENGTH: 12
<212> TYPE: PRT
<213> ORGANISM: Hepatitis C virus

<400> SEQUENCE: 97

Ser Val Ala Ser Ser Ala Ser Gln Leu Ser Ala
1               5                   10

<210> SEQ ID NO 98
<211> LENGTH: 9
<212> TYPE: PRT
<213> ORGANISM: Hepatitis C virus

<400> SEQUENCE: 98

Arg Asp Trp Ala His Asn Gly Leu Arg
1               5

<210> SEQ ID NO 99
<211> LENGTH: 9
<212> TYPE: PRT
<213> ORGANISM: Hepatitis C virus

<400> SEQUENCE: 99

Leu Arg Asp Trp Ala His Asn Gly Leu
1               5

<210> SEQ ID NO 100
<211> LENGTH: 12
<212> TYPE: PRT
<213> ORGANISM: Hepatitis C virus

<400> SEQUENCE: 100

Pro Leu Arg Asp Trp Ala His Asn Gly Leu Arg Asp
1               5                   10
```

EPITOPES OF HEPATITIS C VIRUS

PRIORITY CLAIM

This application claims priority to provisional patent application 60/381,273 filed May 16, 2002, the entire contents of which are hereby incorporated by reference.

STATEMENT AS TO FEDERALLY SPONSORED RESEARCH

This invention was made with U.S. Government support under a National Institutes of Health grant number AI31563. The government has certain rights in the invention.

BACKGROUND OF THE INVENTION

The invention relates to T cell immunity to viral antigens.

Hepatitis is a disorder involving inflammation of the liver. Hepatitis C (HCV) is a form of hepatitis caused by an RNA virus. This pathogen accounts for many of the hepatitis cases previously referred to as non-A, non-B hepatitis. HCV is believed to cause between 150,000 and 250,000 new cases of hepatitis in the United States each year. Hemophiliacs and drug abusers are at the greatest risk, but anyone can contract the disease. Transmission often occurs through a blood transfusion, administration of blood products that were contaminated with hepatitis C, or by sharing needles with intravenous drug users that were infected with the virus. At present, there is no vaccine to prevent HCV infection in humans.

SUMMARY OF THE INVENTION

The invention provides compositions containing HCV epitopes, which are recognized by cytotoxic T lymphocytes (CTL). Such polypeptides are used in prophylactic vaccines, immunotherapies, and assays to monitor the progress or success of immune interventions. The compositions are optimized to elicit an immune response in a genetically-diverse population of individuals. For example, the composition contains a mixture of HCV peptide epitopes and each individual epitope preferentially binds to specific HLA class I molecule. The mixture is optimized for a given population pool, because the peptides are chosen based on the prevalence or frequency of HLA class I expression in a target population. For example, HLA A2 is a frequently expressed allele in Caucasian populations, but not in non-Caucasian populations. The HLA profiles of various populations is known. Despite its frequency in Caucasian populations, a minority of HLA-A2 positive individuals has detectable HCV-specific CD8+ T cell responses in PBMC towards previously described HLA-A2 epitopes.

Accordingly, the invention provides an immunogenic composition containing a plurality, e.g., at least two, of immunodominant Hepatitis C Virus (HCV) polypeptides, which bind to a plurality of HLA class I molecules. For example, the composition contains a mixture of 2, 3, 4, 5, 10, 20, or more peptides, each of which have been previously determined to bind to a particular HLA class I molecule and stimulate an HCV-specific CTL response. The mixture of CTL-stimulatory HCV peptide epitopes binds to a spectrum of HLA class I molecules which are expressed in a majority of the individuals in a target population. Preferably, the peptide does not bind to HLA A2. At least one polypeptide of the mixture binds to an HLA-A class I molecule, and least one polypeptide binds to an HLA-B or HLA-C class I molecule. At least one polypeptide binds to an HLA class I molecule selected from the group consisting of Cw7, A1, and B55. The spectrum of HLA binding of the peptides is such that the mixture of peptides binds to HLA alleles expressed in at least 85%, more preferably 95%, more preferably 98%, more preferably 99%, and most preferably substantially all individuals in a target population. A target population is identified by a defined set of parameters, e.g., geographic location, ethnicity, age, sex, or race.

The peptides are optimized for size as well as HLA binding. The peptide is as small as possible while still maintaining the immune stimulatory activity of a large peptide from which it was derived. By immune stimulatory activity is meant the ability to bind an appropriate MHC molecule and induce an antigen specific cytotoxic T lymphocyte response. By a cytotoxic T lymphocyte response is meant a CD8+ T lymphocyte response specific for an antigen of interest. Active or stimulated CTLs secrete lymphokines (e.g., interferon-γ) and/or liberate products (e.g., serine esterases) that inhibit viral replication in infected autologous cells or transfected cells, with or without cell killing.

Preferably, the peptides are less than 50 amino acids in length and contain the amino acid sequence of one or more of the following reference sequences: SEQ ID NO:42, 43, 44, 45, 46, 47, 48, 49, 50, 51, 52, 53, 54, 55, 56, 57, or 58. For example, the peptide consists essentially of one or more of the amino acid sequences listed above.

Optimized peptide epitopes include peptides which contain the following amino acid sequences: DYPYRLWHY (SEQ ID NO:42), HCV E2 protein and binds to HLA Cw7; ATDALMTGY (SEQ ID NO:45), HCV NS3 protein and binds to HLA A1; QPEKGGRKPA (SEQ ID NO:47), HCV NS5B protein and binds to HLA B55; and SPGEINRVAA, (SEQ ID NO:48), HCV NS5B protein and binds to HLA B55. Preferably, the epitope binds to HLA A1, e.g., a peptide containing the amino acid sequence of SEQ ID NO:45.

Other useful immunogenic compositions include those which contain polypeptides containing the amino acid sequence of SEQ ID NO:19, 50, 51, 52, 53, 54, 55, 56, 57, and/or 58. The HCV proteins, amino acid coordinates, amino acid sequence, and HLA restriction is provided in Table 9. Preferably, the epitope binds to HLA B35, e.g., a peptide containing the amino acid sequence of SEQ ID NO:49, 55 or 57.

The peptide is a chain of at least four HCV amino acid sequence residues, preferably at least six, more preferably eight or nine, sometimes ten to twelve residues, and usually fewer than about fifty residues, more usually fewer than about thirty-five, and preferably fewer than twenty-five, e.g., eight to seventeen amino acid residues. The sequence is homologous to a corresponding portion of contiguous residues of an HCV protein and contains a CTL-inducing epitope. Preferably, the amino acid sequence of each polypeptide contains at least 8 contiguous amino acids of a naturally-occurring HCV protein region selected from the group consisting of Core, E, NS3, NS4, and NS5. For example, the peptide contains at least 8 contiguous amino acids of an HCV E2, NS3, NS5A, NS5B, or P7 protein. Such peptides and peptide mixtures are useful as vaccines or in immunotherapy approaches for viral infections. A preferred length is 8–10 or 8–12 amino acids.

The polypeptides and nucleic acids described herein for vaccines or vaccine development are substantially pure. By a substantially pure polypeptide is meant a polypeptide, which is separated from those components (proteins and other naturally-occurring organic molecules) which naturally accompany it. A polypeptide is substantially pure when it constitutes at least 60%, by weight, of the protein in the preparation. Preferably, the protein in the preparation is at least 75%, more preferably at least 90%, and most preferably at least 99%, by weight, of the desired peptide. A substantially pure polypeptide is obtained, e.g., by extraction from a natural source; by expression of a recombinant nucleic acid; or by chemically synthesizing the protein. Purity is measured by a number appropriate methods known in the art, e.g., column chromatography, polyacrylamide gel electrophoresis, or HPLC analysis. A protein is substantially free of naturally associated components when it is separated from those contaminants which accompany it in its natural state. Thus, a protein which is chemically synthesized or produced in a cellular system different from the cell from which it naturally originates will be substantially free from its naturally associated components.

In addition to peptides, the invention encompasses nucleic acids, e.g., oligonucleotides, which encode the immunogenic HCV peptide epitopes. The nucleic acids, e.g., DNA or RNA, are substantially pure. By substantially pure DNA is meant DNA that is free of the genes which, in the naturally-occurring genome of the organism from which the DNA of the invention is derived, flank the desired gene sequence. The term therefore includes, for example, a recombinant DNA which is incorporated into a vector, into an autonomously replicating plasmid or virus, or into the genomic DNA of a prokaryote or eukaryote at a site other than its natural site; or which exists as a separate molecule (e.g., a cDNA or a genomic or cDNA fragment produced by PCR or restriction endonuclease digestion) independent of other sequences.

A method of inducing a cytotoxic T cell immune response is carried out by contacting a CTL with an immunogenic HCV peptide epitope to stimulate the CTL to produce cytokines and/or kill a virally-infected cell. The CTL or heterogenous population of cells containing a CTL, e.g., peripheral blood mononuclear cells (PBMC), are contacted with peptide ex vivo or in vivo. For vaccine purposes, the peptide epitope or mixture of peptide epitopes is previously determined, and the peptide and mixture is administered to a wide range of individuals prior to a known exposure to a viral pathogen. For immunotherapeutic approaches, each individual, e.g., a virally-infected patient, may be tested to identify strongly immunogenic HCV epitopes, thereby customizing the peptide or mixture of peptides to be administered for the purpose of reducing an existing infection. For example, PBMC from a chronically-infected individual are contacted with a peptide matrix representing all HCV proteins to identify immunogenic HCV epitopes for the patient's HLA type, thereby yielding a customized immunogenic composition. Following identification of epitopes, a customized immunogenic is administered to the patient in vivo or to the patient's immune cells ex vivo.

The invention also encompasses preferentially stimulating an early memory HCV specific CD8+ T-cell response. For example, the method preferentially induces proliferation of T cells with the following phenotype: double positive for CD27 and CD28, and low in CD45RA. The phenotype is further characterized as being CCR7 positive; preferably, the phenotype is characterized by high expression of CCR7 compared to unstimulated cells. Accordingly, the method includes a step of contacting a population of T cells with one or more of the peptide antigens described above to increase proliferation of an early memory HCV specific CD8+ T cell. For example, a method of stimulating an HCV-specific immune response is carried out by administering to a mammal an immunogen comprising a peptide epitope selected from the group consisting of SEQ ID NO: 42, 43, 44, 45, 46, 47, 48, 49, 50, 51, 52, 53, 54, 55, 56, 57, and 58. The method leads to an increase in the number (or the level of proliferation) of HCV-specific early memory CD8+ T cells compared to that prior to administration of the immunogen.

The method also includes a method for measuring an immune response in a patient, e.g., for the purpose of monitoring the success of immune interventions. The method is carried out by providing a sample of cytotoxic T lymphocyte effector cells from a patient, e.g., patient who has been previously immunized with an HCV polypeptide; providing HLA class I matched detectably-labelled target cells, e.g., target cells are labeled with $^{51}Cr$ and are have been pulsed with an HCV polypeptide; allowing the effector cells and target cells to come into contact, e.g., in culture; and determining the amount of label released by the target cells. An increase in the amount of label released compared to a control value indicates the presence of an HCV-specific immune response in said patient. A control value is a value obtained from testing the patient prior to administration of a vaccine peptide or a value obtained from a pool of uninfected or unstimulated individuals.

The peptides are prepared synthetically or by recombinant DNA technology. The term peptide is used interchangeably with polypeptide in the present specification to designate a series of amino acids connected one to the other by peptide bonds between the alpha-amino and alpha-carboxy groups of adjacent amino acids. Optionally, one or more peptide bonds are replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic yields a peptide mimetic, which is more stable and thus more useful as a therapeutic. Such mimetics, and methods of incorporating them into peptides, are well known in the art. Similarly, the replacement of an L-amino acid residue is a standard way of rendering the peptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. The polypeptides or peptides are either in their neutral (uncharged) forms or in forms, which are salts, and either free of modifications such as glycosylation, side chain oxidation, or phosphorylation or containing these modifications, subject to the condition that the modification not destroy the immune stimulatory activity of the polypeptides.

Derivative peptide epitopes have an amino acid sequence, which differs from the amino acid sequence of a naturally-occurring HCV peptide. Such derivative peptides have at least 50% identity compared to a reference sequence of amino acids, e.g., a naturally-occurring HCV peptide. Preferably, a derivative is 90, 95, 98, or 99% identical to a naturally-occurring HCV protein sequence. The derivative contains a conservative amino acid substitution. By conservative substitutions is meant replacing an amino acid residue with another which is biologically and/or chemically similar, e.g., one hydrophobic residue for another, or one polar residue for another. The substitutions include combinations such as Gly, Ala; Val, Ile, Leu; Asp, Glu; Asn, Gln; Ser, Thr; Lys, Arg; and Phe, Tyr. Nucleotide and amino acid comparisons described herein are carried out using the Lasergene software package (DNASTAR, Inc., Madison, Wis.). The MegAlign module used is the Clustal V method (Higgins et al., 1989, CABIOS 5(2):151–153). The parameter used is gap penalty 10, gap length penalty 10.

Other embodiments and features of the invention will be apparent from the following description thereof, and from the claims.

BRIEF DESCRIPTION OF THE DRAWINGS

FIGS. 1B–G are a series of histograms showing the results of a tetramer analysis as shown for an exemplary subject, subject P6 (shown in FIG. 1A).

FIGS. 3C–G are histograms showing the results of an ICS assay showing that peptide 951–970 was presented by HLA B37.

FIG. 3H is a photograph of the results of an Elispot assay defining a minimal epitope of peptide 951–970.

FIGS. 5A–H are a series of histograms showing the results of a tetramer analysis before and after stimulation of PBMC with peptides representing HCV epitopes. In subject P14, only one of four tetramers (NS3 1073) tested positive directly ex vivo. After 9 days of stimulation with the four respective peptides, 3 of four tetramers tested positive, with frequencies up to 30% of CD8+ T cells.

FIG. 6A is a bar graph showing HCV-specific CD8+ T-cell responses from a representative patient. Using an ELISpot matrix spanning, the entire HCV genome was comprehensively mapped. The strength and specificity of the HCV-specific CD8+ T-cell response was determined for each individual. Responses in a representative patient R5 is shown in FIG. 6A. The epitopes targeted are plotted beneath the corresponding position in the HCV genome map and the magnitude of the response (SFC=spot forming cells) is given. Subject R5 targeted 6 different epitopes, one located in E1, one in NS3, two in NS4 and two in NS5.

FIGS. 6B–C are dot plots showing a CD8+ T-cell response directed against peptide 174D. Strong responses, such as the one directed against the peptide 174 D could be confirmed in a direct ex-vivo ICS. An irrelevant peptide was used as a control (FIG. 6C) in the same assay.

FIG. 6D is a dot plot showing responses using a peptide-specific T-cell line (following a single round of peptide stimulation) to confirm that T cell responses were CD8+.

FIG. 6E is a bar graph showing a definition of the HLA restriction of the epitope using partially HLA matched and mismatched heterologous B cell lines.

FIGS. 7A–G are dot plots showing an ex vivo HCV tetramer response. Tetramers were custom synthesized for 7 different HCV epitopes, restricted by 4 different HLA alleles and cells were stained ex vivo. The percentage of tetramer+ cells/total CD8+ cells is given in the upper right panel of each dot plot. Even for responses with a low frequency, clouds large enough for phenotyping were generated through the acquisition of large quantities of blood at the time of donation.

FIGS. 8A–F are dot plots showing that HCV-specific CD8+ T-cells can proliferate and lyse target cells in vitro. HCV-specific CD8+ T-cells from subjects with resolved as well as chronic infection were expanded upon 10–14 days following a single round of peptide stimulation. The % of IFN-γ+ cells/total cells following expansion is given in the upper right panel of each dot plot. The percentage of IFN-γ+ cells detected using the same epitope in the ex vivo ELISpot is given in parenthesis.

FIGS. 8G–L are bar graphs showing that the cell lines specifically lysed peptide pulsed targets in a standard 4 hour chromium release assay at an effector: target ratio 30:1.

FIGS. 11A–L are dot plots showing the phenotype of HCV-specific CD8+ T cells. Surface expression pattern of HCV-specific CD8+ T-cells was analyzed using antibodies for CD45RA, CD27, CD28 and CCR7 and is shown for 3 epitopes in 2 representative patients (C2 and R3). The panels on the left show the expression of CD27 and CD28 within the total CD8+ T-cell population and the tetramer positive cells alone. The panels on the right show CD45 RA and CCR7 expression in the tetramer + and − populations. The two upper rows are representative examples for the phenotype seen in both chronic and resolved subjects. In contrast, the lower row shows the staining for a unique response in a single patient with a distinct phenotype. The middle and lower row are different epitopes recognized by the same individual with resolved infection.

DETAILED DESCRIPTION

Figure 1A:
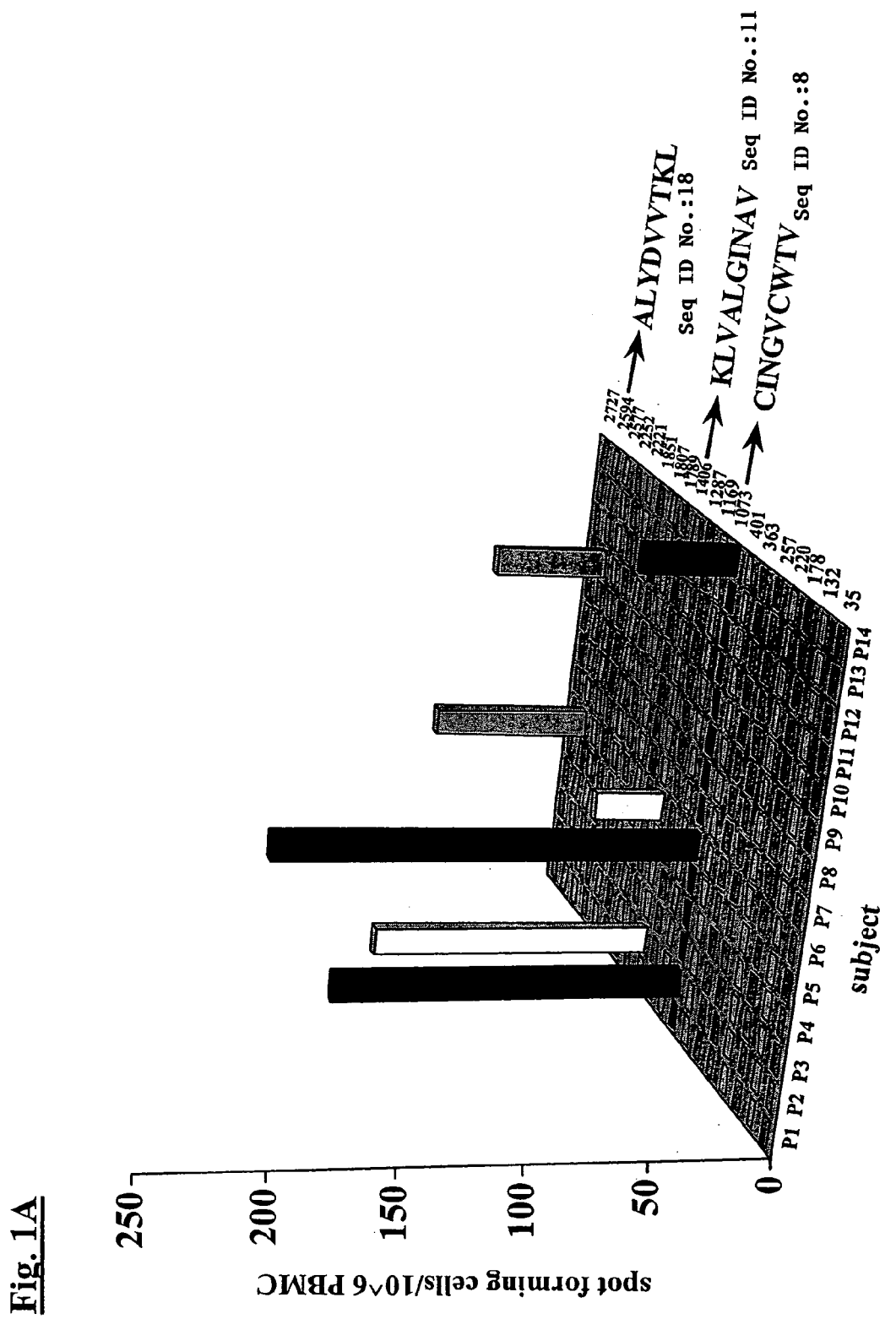
FIG. 1A is a bar graph showing the magnitude and breadth of the HCV-specific CD8+ T cell responses using HLA A2 restricted peptides in an Elispot assay.

The HCV-specific CD8+ T-cell response plays a critical role in protecting against and combating hepatitis C-virus infection. Prior to the invention, studies of these responses relied on the analysis of a small number of predicted HCV epitopes, mostly restricted by HLA A2. In order to determine the actual breadth and magnitude of CD8+ T-cell responses in the context of diverse HLA class I alleles, a comprehensive analysis of responses to all expressed HCV proteins was carried out. A panel of 301 overlapping peptides was used to analyze PBMC from a cohort of 14 anti-HCV positive, HLA A2 positive individuals in an Elispot assay. Only 4 subjects had detectable HLA A2 restricted responses in PBMC, and only 3 of 19 predicted A2 epitopes were targeted, all of which were confirmed by tetramer analysis. In contrast, 9 of 14 persons had responses by more comprehensive analysis, with many responses directed against previously unreported epitopes. These results indicate that circulating HCV-specific CD8+ T-cell responses were detected in PBMC in the majority of infected persons, and that these responses are heterogeneous with no immunodominant epitopes being consistently recognized. As responses to epitopes restricted by single HLA alleles such as HLA A2 do not predict the overall response in an individual, more comprehensive approaches, as reported herein, define the role of the CD8+ T-cell response in HCV infection. The low level or absence of responses to many predicted epitopes provides rationale for immunnotherapeutic interventions to broaden CTL recognition.

HCV-specific Immune Responses

The immune system of some individuals is able to terminate infection with the hepatitis C virus. The response is mediated by HCV-specific cytotoxic T cells. An important feature of prophylactic HCV vaccines or immunobased therapies described herein is the induction of such HCV-specific CTL.

CTL recognize small regions of HCV (typically 8–10 amino acids long), called CTL epitopes. The recognition is also dependant on the expression of certain molecules (HLA class I). Individuals have each a different set of HLA alleles, and only persons who express the HLA allele by which a specific epitope is restricted will be able to develop a CTL response targeting it. Vaccines and other immunobased therapies must be effective in a genetically heterogeneous population. Unlike previous vaccines and immunobased therapies, the epitopes described herein elicit CTL responses restricted by broad range of HLA alleles as possible. To this end, detailed knowledge of the exact length and sequence of HCV epitopes and of their HLA restriction is necessary as the basis for the development of HCV vaccines and immunotherapies and for the development of assays to measure the success of these interventions.

So far, only a limited number of HCV epitopes have been described in detail, with the majority being presented by the HLA A2 molecule. This HLA allele is only present in a minority of individuals in the US and worldwide. Therefore the previously defined epitopes fail to induce an immune response in most people. More epitopes restricted by broad range HLA alleles expressed in a target population need to be defined in order to generate vaccines or other immunobased therapies which are applicable to a broad range of infected individuals or individuals at risk of developing an HCV infection. The compositions described herein contain peptides, which bind to a variety of HLA class I molecules, which are expressed and well represented in many populations or are optimized for administration to a defined target population.

Therapeutic Administration

Polypeptides (or nucleic acids encoding the peptides) described herein are useful to induce HCV-specific CTL for the purpose of preventing infection or combating an existing infection. When a peptide is used as a vaccine, it is administered to a patient in the form of a peptide solution in a pharmaceutically acceptable carrier. Standard methods for delivery of peptides are used, e.g., for intracellular delivery, the peptides are packaged in liposomes. Such methods are well known to those of ordinary skill in the art. The peptides are administered at an intravenous dosage of approximately 1 to 100 μmoles of the polypeptide per kg of body weight per day. The compositions of the invention are useful for parenteral administration, such as intravenous, subcutaneous, intramuscular, and intraperitoneal. For example, a unit dose of the peptide ranges from 0.1 to 100 mg, which may be administered at one time or repeatedly to a patient. A plurality of peptides are optionally administered together (simultaneously or sequentially). The peptides in the mixture bind to different HLA class I molecules to yield a vaccine that elicits a CTL response in the majority of individuals in a genetically diverse population.

Peptides are recombinantly produced or synthetically made using known methods. Peptide solutions are optionally lyophilized or granulated with a vehicle such as sugar. When the compositions are administered by injection, they are dissolved in distilled water or another pharmaceutically acceptable excipient prior to the injection. The peptides are used to induce a HCV-specific CTL response in vivo or ex vivo. The peptides are administered directly to an individual or lymphocytes (e.g., derived from peripheral blood mononuclear cells) are removed from an individual, cultured with one or more peptides, and returned to the individual. For example, 0.01 to 1 mg of the peptide is added to $10^7$ to $10^9$ peripheral blood lymphocytes obtained from a patient, then the cells are cultivated for several hours to one day. The cells are then introduced back into the patient. In such ex vivo therapy, cell stimulation is performed outside the body. For example, lymphocytes or other target cells are removed from a patient and contacted with immunogenic peptides, providing a stimulatory concentration of peptide in the cell medium far in excess of levels which could be accomplished or tolerated by the patient. Following treatment to stimulate the CTLs, the cells are returned to the host to treat a viral infection. The host's cells may also be exposed to vectors which carry nucleic acids encoding the peptides. The ex vivo stimulated cells are returned to the patient after reaching a predetermined cell density.

Alternatively, the cells are continuously cultivated in vitro in a culture medium to which recombinant interleukin 2 and 1 μg/ml of the peptide has been added. The cells are cultured over several hours, days, or several weeks to induce CTL. Activated CTL are then intravenously injected into the patient.

DNA encoding a peptide epitope may also be administered, e.g., by incorporating the DNA into a viral vector. Nucleic acids are administered using known methods, e.g., intravenously, at a dose of approximately $10^6$ to $10^{22}$ copies of the nucleic acid molecule.

A pharmaceutical composition contains a pharmaceutically-acceptable excipient and optionally contains a composition, which primes CTL, e.g., a lipid such as tripalmitoyl-S-glycerylcysteinly-seryl-serine. The concentration of CTL stimulatory peptides ranges from less than about 0.1%–1% to as much as 20 to 50% or more by weight, depending on mode of administration selected. Dosage determination and excipient choice is well within the skill of those practicing in the art of medicine and pharmaceuticals.

Vaccine compositions containing immunodominant CTL stimulatory peptides are administered to a patient susceptible to or otherwise at risk of HCV infection to enhance the patient's own immune response capabilities. An immune stimulatory dose is one that increases the level of antigen-specific immunity compared to the level prior to immunization. For example, peptides are administered at a dose of 1.0 µg to about 500 mg per 70 kilogram patient, more commonly from about 50 µg to about 200 mg per 70 kg of body weight. The peptides are administered to individuals of an appropriate HLA type. Alternatively, a mixture of peptides is administered. Individual peptides bind to a specific HLA class I molecules; however, the binding specificity of the mixture encompasses several frequently expressed haplotypes to ensure a broad CTL response in a diverse population of individuals.

Breadth and Specificity of HCV-specific CD8+ T Cell Immunity

HCV-specific CTL responses against selected HLA-A2 restricted epitopes are not indicative of the total response. Accordingly, a comprehensive analysis of all HCV proteins was undertaken to examine the breadth and specificity of CD8+ T cell responses against HCV. An Elispot assay was used to determine the recognition of a panel of peptides spanning all expressed HCV proteins. The relative contribution of HLA A2 and non-HLA A2 alleles in presenting viral proteins for recognition by CD8+ T cells was evaluated. The overall magnitude and breadth of HCV-specific responses was determined using PBMC taken from HCV infected individuals.

14 anti-HCV positive individuals were selected for study based on expression of the HLA A2 allele (Table 1).

TABLE 1

| SUBJECT | DISEASE | RNA | HCV GT | HLA |
|---|---|---|---|---|
| P0 | Resolved HCV | neg. | ND | A2, 25 B37, 44 Cw5, 6 |
| P1 | acute HCV | >1,000000 | 1b | A1, 2 B8, 44 Cw5, 7 |
| P2 | acute HCV | 599,000 | 1b | A1, 2 B40, 57 Cw7, 15 |
| P3 | Resolved HCV | neg | ND | A2, 29 B44 Cw16 |
| P4 | Resolved HCV | neg | ND | A2, 3 B7, 60 Cw7 |
| P5 | chronic HCV | 357,169 | 2 | A2, 11 B55, 62 Cw1, 9 |
| P6 | chronic HCV | 7,718 | 2a/c | A1, 2 B37, 44 Cw5, 6 |
| P7 | chronic HCV | 67,051 | 1a | A1, 2 B8, 55 Cw3, 7 |
| P8 | chronic HCV | 456,490 | 2b | A2, 29 B18, 40 Cw3, 5 |

TABLE 1-continued

| SUBJECT | DISEASE | RNA | HCV GT | HLA |
|---|---|---|---|---|
| P9 | chronic HCV | 33,637 | 2b | A2, 3 B39, 44 Cw7, 16 |
| P10 | chronic HCV | 506,420 | 1b | A2, 32, B40 Cw3 |
| P11 | chronic HCV | 1,213,300 | 3a | A2, 29 B44, 50 Cw4, 16 |
| P12 | chronic HCV | 996,000 | 1a | A1, 2 B8, 44 Cw1 |
| P13 | chronic HCV | >1,000,000 | 1a | A2, 24 B8, 41 Cw7, 17 |
| P14 | chronic HCV | 159,320 | 2b | A1, 2 B7, 8 Cw7 |

Alleles for which optimal epitopes were tested are in bold letters

One additional subject (P0) had been previously studied and shown to have CTL responses by limiting dilution cloning. This person had acute HCV infection in 1998 followed by spontaneous clearance of the virus. Contemporary samples were used for comparative assessment of immune responses using overlapping peptides. HLA typing of each individual was performed using standard serological and molecular techniques. HCV epitopes were evaluated as follows.

Synthetic peptides were made using standard methods. The peptide sequences correspond to the HCV 1a subtype. Polypeptides were synthesized as COOH-terminal free acids on a Synergy 432A peptide synthesizer (Applied Biosystems, Foster City, Calif.). Peptides were 20 amino acids in length, overlapping adjacent peptides by 10 amino acids. Fine mapping was achieved using additional smaller peptides. All peptides were reconstituted in sterile RPMI 1640 medium containing 10% dimethylsulfoxide (Sigma Chemical Co.) and 1 mM dithiothreitol (Sigma Chemical Co.).

Elispot assays were carried out using known methods. For example, 96-well polyvinylidene plates (Millipore) were coated with 2.5 µg/ml recombinant human anti-IFN-γ antibody (Endogen) in PBS at 4° C. overnight. Fresh or previously frozen PBMC were added at 200,000 cells/well in 140 µl R10 medium (RPMI 1640 [Sigma-Aldrich], 10% FCS [Sigma-Aldrich], and 10 mM Hepes buffer [Sigma-Aldrich] with 2 mM glutamine and antibiotics [50 U/ml penicillin-streptomycin]). Peptides were added directly to the wells at a final concentration of 10 µg/ml. The plates were incubated for 18 hours at 37° C., 5% $CO_2$. Plates were then washed, labeled with 0.25 µg/ml biotin-labeled anti IFN-γ (Endogen), and developed by incubation with streptavidin-alkaline phophatase (Bio-Rad) followed by incubation with BCIP/NBT (Bio-Rad) in Tris-buffer (pH 9.5). The reaction was stopped by washing with tap water and the plates were dried overnight, prior to counting on an Elispot reader (AID, Strassberg, Germany). The background was always below 15 spot-forming cells (SFC)/$10^6$ PBMC. Responses were considered positive if the number of spots per well minus the background was at least 25 SFC/$10^6$ PBMC, PHA served as a positive control.

HLA class I-peptide tetramer staining of cells was carried out as follows. HLA class I-peptide tetramers were prepared using known methods, e.g., the method described by Lechner et al., 2000, J. Exp. Med. 191:1499–1512. The following tetramers were prepared for analysis: tetramers specific for 6 epitopes restricted by HLA-A2 (core peptide 35–44, YLLPRRGPRL (SEQ ID NO:1); NS3 peptide 1073–1081, CINGVWCTV (SEQ ID NO: 8); NS4 peptide 1406–1415, KLVALGINAV (SEQ ID NO:11); NS4 peptide 1807–1816, LLFNILGGWV (SEQ ID NO:13); NS4 peptide 1851–1859, ILAGYGAGV (SEQ ID NO:14); NS5B peptide 2594–2602, ALYDVVTKL (SEQ ID NO:18). 0.5 to 1 million PBMC were stained using known methods, e.g., the method described by Gruener et al., 2001 J. Virol. 5550–5558. Flow cytometric analysis was performed with a Becton Dickinson FACSCalibur fluorescence-activated cell sorter, and data analysis was performed with CellQuest software. Staining was considered positive if tetramer-positive cells formed a cluster distinct from the tetramer negative cells and the frequency of tetramer positive cells was greater than 0.02% of the total CD8+ population.

Intracellular cytokine staining (ICS) for interferon-γ was performed using methods known in the art, e.g., the method described by Altfeld, 2001, J. Immunol. 167:2743–2752. 1×10⁶ PBMC were incubated with 4 μM peptide and anti-CD28 and anti-CD49d MAbs (1 μg/ml each; Becton Dickinson) at 37° C. The cells were cultured in a 5% $CO_2$ incubator for 1 h before the addition of Brefeldin A (1 μl/ml; Sigma-Aldrich). The cells were then incubated for an additional 5 h at 37° C. and 5% $CO_2$. PBMC were washed and stained with surface antibodies, antigen-presenting cell-conjugated anti-CD3 and phycoerythrin-conjugated anti-CD8 (Becton Dickinson) at room temperature for 20 min. Following the washing, the PBMC were fixed and permeabilized (Caltag, Burlingame, Calif.), and the fluorescein isothiocyanate-conjugated anti-IFN-γ MAb (Becton Dickinson) was added. Cells were then washed and analyzed on a FACS-Calibur flow cytometer using CELLQuest software (Becton Dickinson). For HLA restriction, partially HLA matched heterologous BCL were pulsed with 10 μg of peptide for an hour, washed three times with R10, and then 2×10⁵ of the BCL were added to the T-cell line instead of peptide.

Peripheral blood mononuclear cells were stimulated in bulk. For establishing CTL lines, cryopreserved or fresh PBMC (4–10×10⁶) were stimulated with 1 μg/ml of synthetic HCV peptide and 0.5 μg/ml of the costimulatory antibodies anti-CD28 and anti-CD49d (Becton Dickinson) in R-10. Irradiated feeder cells (20×10⁶ allogeneic PBMC) were added to the culture in a 25-cm² culture flask (Costar, Cambridge, Mass.). Recombinant interleukin-2 (25 U/ml) was added on day 2 and twice a week thereafter. Expansion of peptide-specific cells for tetramer staining was done by culturing 5×10⁶ PBMC pulsed with 10□g of each of four peptides for 8 or 9 days in R-10 containing 25 U/ml interleukin-2.

Once a peptide epitope has been identified, the HLA restriction element of the response is determined using standard methods. For example, the method involves incubating the stimulated PBMC or short term cell lines thereof with a panel of (labeled) target cells of known HLA types which have been pulsed with the peptide of interest, or appropriate controls. The HLA allele(s) of cells in the panel which are lysed by the CTL are compared to cells not lysed, and the HLA restriction element(s) for the cytotoxic T lymphocyte response to the antigen of interest is identified.

Standard cytotoxicity assays were carried out as follows. Autologous B-LCL were pulsed with 10 μg of peptide and $NA_2$ [$^{51}$Cr]$O_4$ (New England Nuclear, Boston, Mass.), and incubated for one hour at 37° C. in 5% $CO_2$. The B-LCL target cells were washed three times with cold R-10 medium and incubated with effector cells at 37° C. for 4 h in three replicate wells. Cellular release of [$^{51}$Cr]$O_4$ into the supernatant was measured using a Top Count Microplate scintillation counter (Packard Instrument Company, Meriden, Conn.), and the percent specific cytotoxicity was calculated by the formula % lysis=[(experimental release−spontaneous release)/(maximum release−spontaneous release)]×100. Results were reported as the mean of triplicate values.

Statistical analysis (Mann-Whitney rank sum test and correlation coefficient) was performed using GraphPad Prism® 3.0a for Macintosh.

A Minority of HLA-A2 Positive Individuals has Detectable HCV-specific CD8+ T Cell Responses in PBMC Towards Previously Described HLA-A2 Epitopes An HCV-specific CD8+ response against HLA A2 epitopes was analyzed. A cohort of 14 anti-HCV positive individuals who expressed the class I allele A2 were examined to determine the relative frequency of responses to reported and predicted epitopes restricted through this common HLA allele. Initially, 19 peptides representing all previously reported HCV-specific, HLA-A2 restricted epitopes, were used (Table 2). Epitopes for which the HLA restriction and the optimal peptide have been defined using T cell clones (by testing partially HLA matched BCL and shorter and longer peptides in dilution rows) indicated with an asterisk.

TABLE 2

Tested HCV epitopes

| HLA | HCV PROTEIN | aa | SEQUENCE | SEQ ID NO: |
|---|---|---|---|---|
| A2 | Core | 35–44 | YLLPRRGPRL | 1 |
| A2 | Core | 132–140 | DLMGYIPLV | 2 |
| A2 | Core | 178–187 | LLALLSCLTV | 3 |
| A2 | E1 | 220–227 | ILHTPGCV | 4 |
| A2 | E1 | 257–266 | QLRRHIDLLV | 5 |
| A2 | E1 | 363–371 | SMVGNWAKV | 6 |
| A2 | E2 | 401–411 | SLLAPGAKQNV | 7 |
| A2 | NS3 | 1073–1081 | CINGVCWTV | 8* |
| A2 | NS3 | 1169–1177 | LLCPAGHAV | 9 |

TABLE 2-continued

Tested HCV epitopes

| HLA | HCV PROTEIN | aa | SEQUENCE | SEQ ID NO: |
|---|---|---|---|---|
| A2 | NS3 | 1287–1296 | TGAPVTYSTY | 10 |
| A2 | NS3 | 1406–1415 | KLVALGINAV | 11* |
| A2 | NS4B | 1789–1797 | SLMAFTAAV | 12 |
| A2 | NS4B | 1807–1816 | LLFNILGGWV | 13 |
| A2 | NS4B | 1851–1859 | ILAGYGAGV | 14 |
| A2 | NS5A | 2221–2231 | SPDAELIEANL | 15* |
| A2 | NS5A | 2252–2260 | ILDSFDPLV | 16 |
| A2 | NS5B | 2577–2586 | RLIVFPDLGV | 17 |
| A2 | NS5B | 2594–2602 | ALYDVVTKL | 18* |
| A2 | NS5B | 2727–2735 | GLQDCTMLV | 19 |
| A3 | NS5B | 2510–2518 | SLTPPHSAK | 20* |
| A3 | NS5B | 2588–2596 | RVCEKMALY | 21* |
| A11 | CORE | 1–9 | MSTNPKPQK | 22* |
| A11 | E2 | 621–628 | TINYTIFK | 23* |
| A11 | NS3 | 1261–1270 | TLGFGAYMSK | 24* |
| A11 | NS3 | 1636–1643 | TLTHPVTK | 25* |
| A24 | NS3 | 1031–1039 | AYSQQTRGL | 26* |
| A29 | NS2 | 827–834 | MALTLSPY | 27 |
| B7 | Core | 41–49 | GPRLGVRAT | 28* |
| B7 | Core | 110–118 | DPRRRSRNL | 29 |
| B8 | NS3 | 1395–1403 | HSKKKCDEL | 30* |
| B8 | NS3 | 1611–1618 | LIRLKPTL | 31* |
| B37 | NS2 | 957–964 | RDWAHNGL | 32* |
| B37 | NS4B | 1966–1976 | SECTTPCSGSW | 33* |
| B44 | Core | 88–96 | NEGCGWAGW | 34 |
| B50 | E2 | 569–578 | CVIGGAGNNT | 35* |
| B57 | NS5B | 2629–2637 | KSKKTPMGF | 36* |
| B60 | Core | 28–37 | GQIVGGVYLL | 37* |
| B60 | E2 | 530–539 | GENDTDVFVL | 38* |
| B60 | E2 | 654–662 | LEDRDRSEL | 39* |
| B60 | NS5A | 2152–2160 | HEYPVGSQL | 40* |
| B60 | NS5A | 2267–2275 | REISVPAEIL | 41* |

Figure 1H:
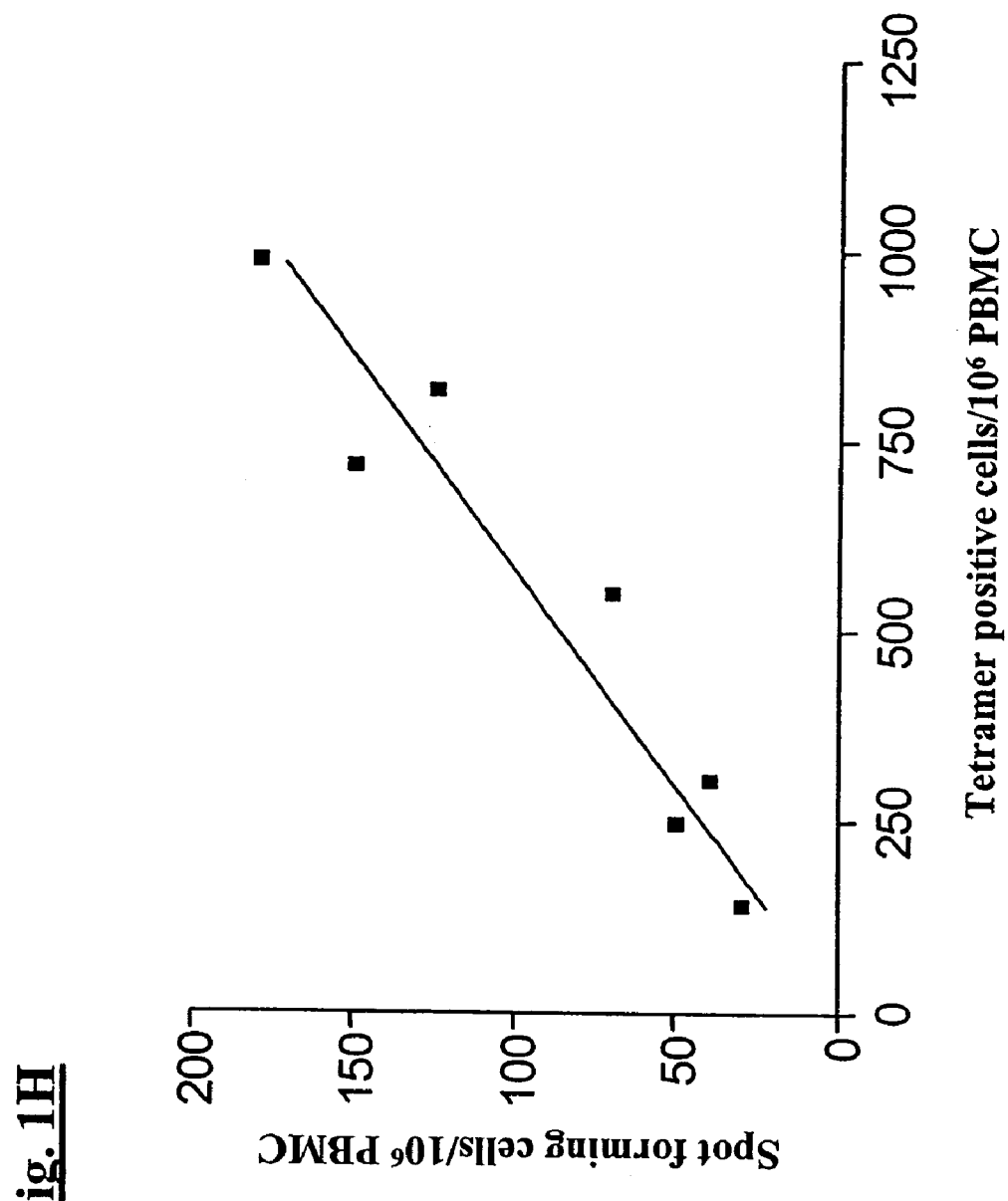
FIG. 1H is a line graph showing a correlation between data derived from an Elispot assay and a tetramer assay.

FIG. 1A shows the magnitude and breadth of the HCV-specific CD8+ T cell responses as detected using 19 different previously described HLA A2 restricted peptides in an Elispot assay. Individual epitopes tested are indicated by the numbering of the first amino acid in the HCV 1a sequence, and magnitudes are shown as IFN-γ spot forming cells/10$^6$ PBMC. Responses were detected only against three of the 19 peptides tested. These results were confirmed by tetramer analysis as shown for subject P6 in FIGS. 1B–G, and results from Elispot and tetramer assay correlated significantly (FIG. 1H).

Responses were detected in PBMC, but only in 4 of the 14 individuals (FIG. 1A). In the four individuals, between 1 and 3 of the epitopes were recognized, and the combined magnitude of these responses ranged between 25 and 285 SFC/$10^6$ PBMC per individual. All HLA-A2 restricted responses were directed against just 3 different epitopes, whereas none of an additional 16 HLA A2 epitopes was recognized by any individual (FIGS. 1A–H).

One possible reason for the lack of detection of HLA A2-restricted CD8+ T cell responses could be cells deficient in interferon-γ expression. In order to assess whether antigen-specific CD8+ T cells were present but not secreting interferon-γ, all individuals were examined by direct visualization of HCV-specific cells using 6 different HLA A2 tetramers (FIGS. 1B–H). Whereas the percentage of positive cells was higher by tetramer analysis than by Elispot assay, all responses detected were confirmed, and no additional responses were seen by tetramer analysis. Furthermore, Elispot and tetramer analysis also correlated well in terms of the magnitude of the responses (FIG. 1H, R=0.91, p<0.001).

Detection of Non HLA A2-restricted CTL Responses in HLA A2-positive Persons

The data shown in FIGS. 1A–H indicate that the minority of HCV seropositive persons have detectable CD8 T cell responses restricted by HLA A2. In order to determine if CD8 T cell responses were present to epitopes other than those predicted to be presented by HLA A2, tests were carried out to detect responses to 22 previously defined non-HLA A2 epitopes (Table 2). Between 0 and 9 (median 3) optimal HCV-specific CTL epitopes restricted by HLA alleles other than A2 were tested per person, depending on HLA type (Table 3).

TABLE 3

HCV epitopes (non-HLA A2) targeted by circulating CD8+ T-cells

| SUBJECT | PEPTIDES TESTED (NUMBER) | PEPTIDES RECOGNIZED |
|---|---|---|
| P1 | core 88, NS3 1395, NS3 1611 (3) | none |
| P2 | NS5B 2629 (1) | none |
| P3 | core 88, NS2 827 (2) | core 88 |
| P4 | core 28, core 41, core 110, E2 530, E2 654, NS5A 2152, NS5A 2267, NS5B 2510, NS5B 2588 (9) | core 41 |
| P5 | core 1, E2 621, NS3 1261, NS3 1636 (4) | none |
| P6 | core 88, NS2 957, NS4B 1966 (3) | none |
| P7 | None (0) | none |
| P8 | NS2 827 (1) | none |
| P9 | core 88, NS5B 2510, NS5B 2588 (3) | none |
| P10 | None (0) | none |
| P11 | core 88, E2 569, NS2 827 (3) | none |
| P12 | core 88, NS3 1395, NS3 1611 (3) | none |
| P13 | NS3 1031, NS3 1395, NS3 1611 (3) | none |
| P14 | core 41, core 110, NS3 1395, NS3 1611 (4) | NS3 1395 |

Each epitope was tested in between 1 and 6 subjects, depending on the prevalence of the respective HLA allele in the cohort. Only 3 subjects had a significant response, each to just one of the peptides (Table 3). Two of the three individuals with a readily detectable response against one of these non-HLA A2 epitopes had tested negative for all 19 HLA A2 peptides. The overall predictive ability of an HLA allele for specific responses was low, as it had been the case for HLA A2 restricted epitopes. For example, of 6 persons expressing HLA B44, only one targeted a previously described B44 epitope. Likewise, none of 5 HLA B8 positive persons targeted either of 2 previously described HLA B8 restricted epitopes, although they recognized other epitopes. These results demonstrate that circulating HCV-specific CD8+ T cell responses are detectable by Elispot in PBMC, but are poorly predicted simply through the HLA type of the host.

Use of Overlapping Peptide Libraries to Confirm and Extend Previously Identified HCV-specific CD8 T Cell Responses CD8+ T cell assays based on predicted or previously reported epitopes detect responses in peripheral blood in only a minority of HCV-infected persons. In order to more comprehensively and directly assess responses, a screening Elispot assay using an HCV protein matrix was developed to examine responses against all expressed proteins. The determination is independent of previous epitope prediction models. An Elispot assay was devised using 301 peptides each 20 amino acids in length and overlapping adjacent peptides by 10 amino acids, thus covering the entire 3011 amino acid HCV 1a polyprotein. To facilitate the analysis, peptides were combined in pools of 10 peptides each with each peptide being contained in two different pools in a matrix setup. This approach allowed for internal controls, as every peptide was present in two different wells, and with 60 wells containing peptide overall, there were many wells without a response serving as standards for a negative response in the presence of peptide.

The feasibility of screening with the peptide matrix was evaluated. The first subject analyzed was designated P0; this subject had been extensively studied previously by limiting dilution assay during resolution of acute infection. A broadly directed CD8+ T cell response had been characterized using this subject. When PBMC were analyzed from this individual more than 2 years after initial infection using the panel of overlapping peptides, responses were detected towards eight 20 mer peptides, which contained 7 of the eight optimal epitopes identified previously through limiting dilution cloning.

Figure 2:
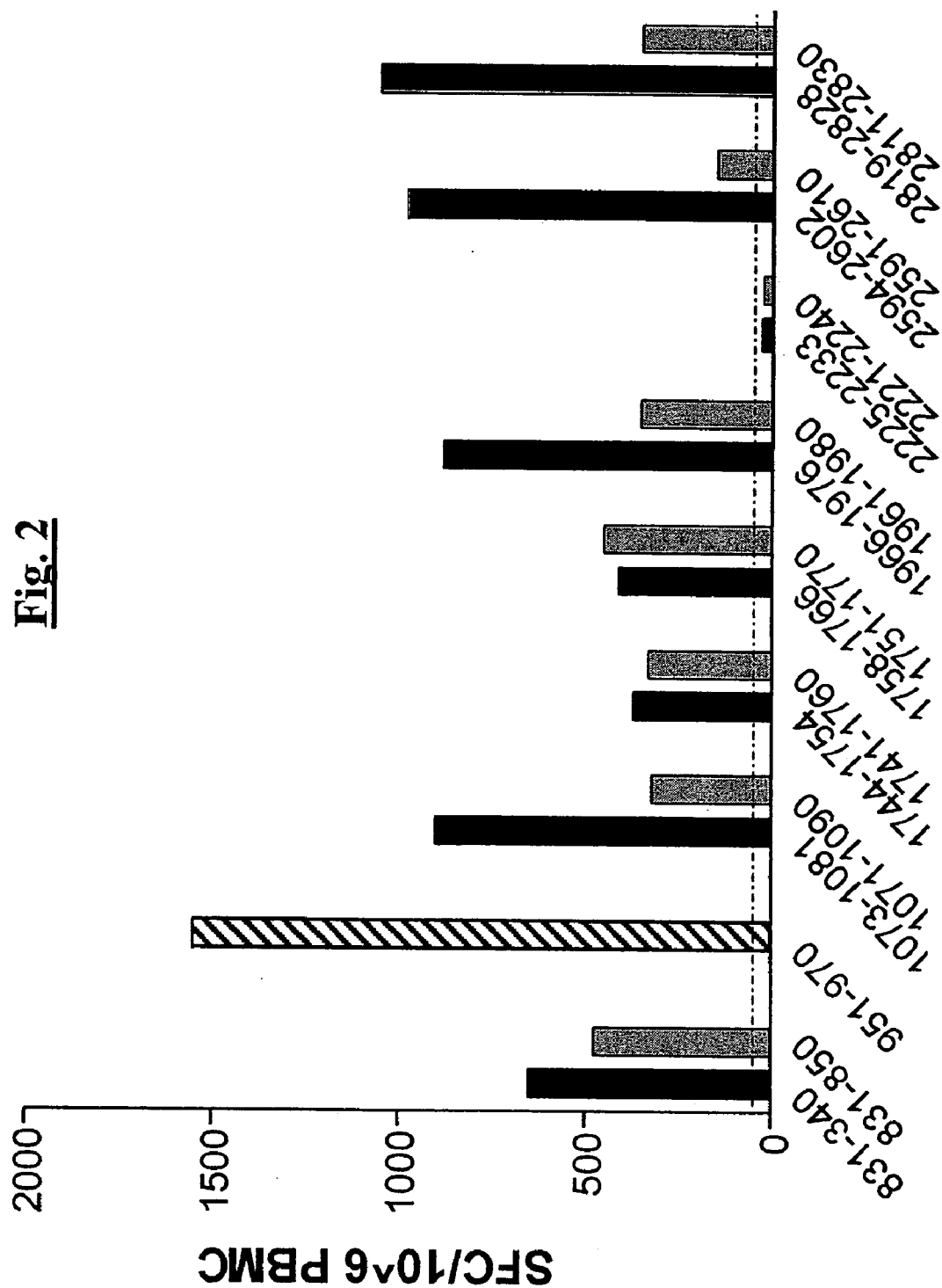
FIG. 2 is a bar graph showing the results of a screening Elispot assay using overlapping 20mer peptides to detect HCV-specific epitopes.
Figure 3B:
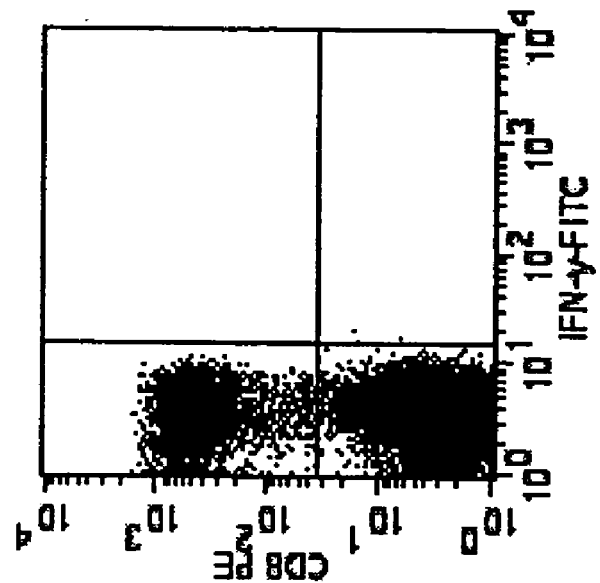
FIGS. 3A–B are histograms showing the results of an intracellular cytokine staining (ICS) assay using PBMC.
Figure 3A:
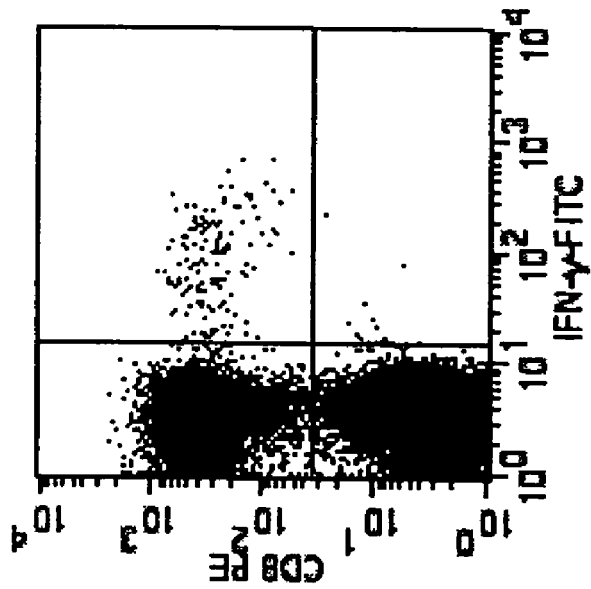

FIG. 2 shows the results of a screening elispot using overlapping 20mer peptides can detect HCV-specific epitopes. During acute infection, 8 different HCV-specific epitopes had been defined from the patient. Responses to 7 of the 8 epitopes were still detectable 2 years after the individual had cleared HCV infection (black bars). When compared with responses to the corresponding 20mer peptides used in the screening Elispot (grey bars), all 7 responses were also detected. However, some of the 20mer peptides elicited responses almost as strong as the optimal epitope, whereas other responses were less vigorous. In addition to the previously described epitopes, a response to an additional peptide was identified (p951–970, striped bar). The magnitude of the responses was lower compared to the time point very early in acute infection, when the CTL clones had been established, but only the response that was lowest in acute infection was no longer detected. Comparison of responses to the 20 mer peptides containing the targeted epitopes to the defined optimal epitopes did demonstrate greater magnitude responses for the optimal epitopes. However, for the one response that was no longer detectable, even the optimal peptide no longer elicited a response, suggesting loss of this weak response over time (peptides 2221–2240 (20 mer) and 2225–2233 (optimal 9 mer) respectively). Another previously described response (NS4B 1744–1754), which was never detected by Elispot in the acute or early phase of infection in this subject, was now detected by using the overlapping 20mer peptides and confirmed using the optimal peptide. Finally, peptide 951–970 was identified; this polypeptide represents an epitope previously not detected in this individual. At the time point studied, this epitope elicited the strongest response of all the nine epitopes. Whether this response was originally not detected because of a lower frequency or because of the different detection techniques used is unclear. ICS data of PBMC confirmed that this peptide was indeed recognized by CD8+ T cells (FIGS. 3A–B). The data shown in FIGS. 3C–G confirmed the response to be class I restricted.

Figure 3I:
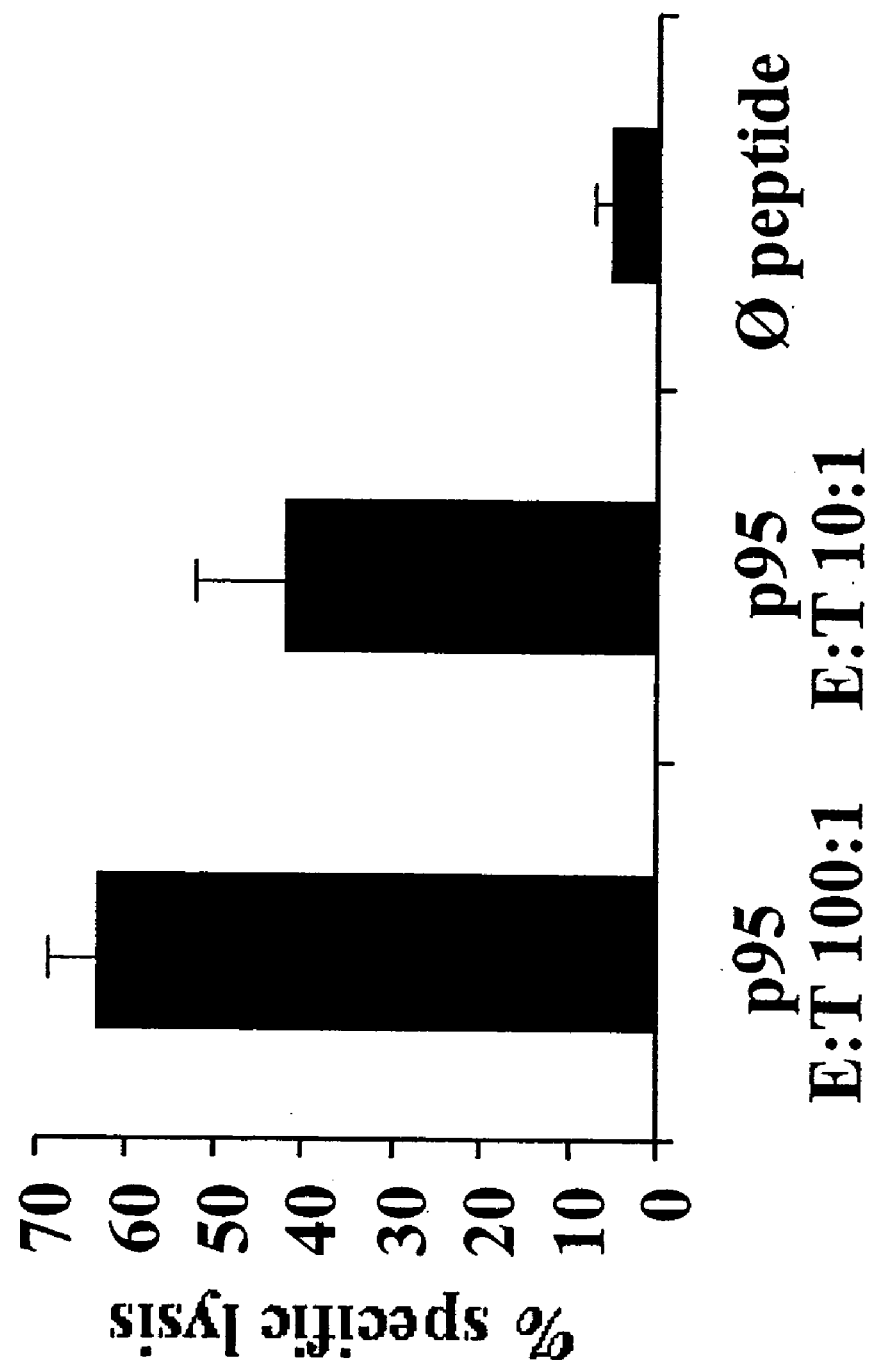
FIG. 3I is a bar graph showing that a T-cell line specific for peptide 951–970 was also capable of mediating specific cytotoxic activity against autologous peptide pulsed B-cells.

Truncated peptides were used to determine the optimal peptide required for recognition (FIG. 3H). The HLA restriction was determined and the minimal peptide to elicit a response was identified. The cells were not only able to secrete interferon-γ upon specific stimulation, but were true cytotoxic T lymphocytes killing peptide pulsed autologous B-cells in a standard chromium release assay (FIG. 3I). These data demonstrate the feasibility of screening for HCV-specific epitopes by an Elispot using overlapping peptides, and that these responses represent CTL. The data also show persistence of polyclonal CTL responses against HCV in a person (P0) with resolved HCV infection.

The Strength and Breadth of the Total HCV-specific CD8+ T Cell Responses is not Predicted by the Responses Against a Limited Number of Epitopes To compare the total response with the response against the predicted epitopes, the screening Elispot approach was applied to the cohort of 14 individuals, resulting in the identification of CTL responses in 9 of 14 persons tested. The method detected not only previously described HLA A2 and non-A2 epitopes (FIG. 4, white and black bars, respectively), but also a total of 9 novel responses in 7 individuals (FIG. 4, grey bars, corresponding peptides listed in Table 4).

TABLE 4

Novel epitopes detected by comprehensive Elispot analysis

| HCV PROTEIN | POSITION | SEQUENCE | HLA | SUBJECT |
|---|---|---|---|---|
| E2 | 610–618 | DYPYRLWHY (SEQ ID NO: 42) | Cw7 | P4 |
| P7 | 781–800 | KWVPGAVYTFYGMWP LLLLL* (SEQ ID NO: 43) | ND | P9, P11, P14 |
| NS3 | 1171–1190 | CPAGHAVGIFRAAVCT RGVA* (SEQ ID NO: 44) | ND | P9 |
| NS3 | 1435–1443 | ATDAL MTGY (SEQ ID NO: 45) | A1 | P2 |
| NS5A | 2191–2210 | ARGSPPSVASSSASQLS APS* (SEQ ID NO: 46) | ND | P12 |
| NS5B | 2568–2577 | QPEKGGRKPA (SEQ ID NO: 47) | B55 | P7 |
| NS5B | 2898–2907 | SPGEINRVAA (SEQ ID NO: 48) | B55 | P7 |

*minimal epitope and HLA-restriction not determined

Figure 4:
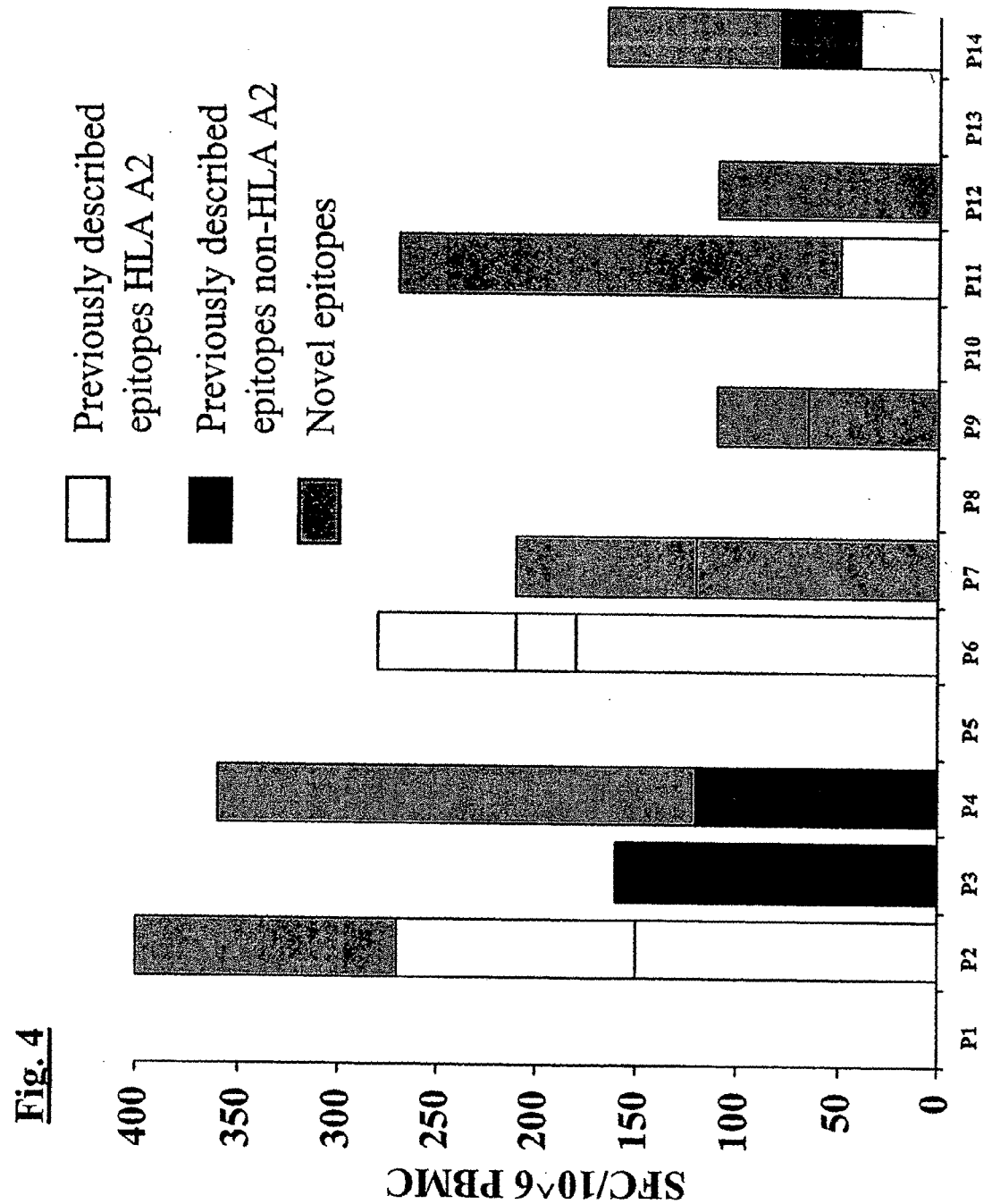
FIG. 4 is a bar graph showing the results of an analysis of the HCV-specific CD8+ T cell response. Elispot responses against previously described HLA-A2 restricted epitopes are shown as white bars, those against previously described non-HLA-A2 restricted epitopes are shown as black bars and novel responses as grey bars.

All responses were confirmed to be CD8+ T cell dependent by CD8+ and CD4+ depletion experiments. Four of the actual epitopes within the larger 20 amino acid peptides were mapped using truncated peptides in a similar Elispot format, and their HLA restriction determined (Table 4). One of the targeted peptides, amino acids 781–800, was recognized by three different persons, whereas 6 of the other newly identified immunogenic peptides were recognized by only one individual. 3 of the 7 individuals (P7, P9, P12) recognizing peptides not previously reported to contain CTL epitopes had no detectable response by the original assay using only the optimal epitopes, and thus would have been erroneously deemed to have no CTL against HCV. In the other four subjects with detectable responses against previously described epitopes, the novel responses comprised between 40% and 80% of the total magnitude of all HCV-specific CD8+ T cell responses together (FIG. 4). There was no significant correlation between the overall magnitude of the novel HCV-specific CD8+ T cell responses and the overall magnitude of the HLA A2 responses or the overall magnitude of the responses towards all previously defined epitopes (p=0.97 and p=0.87, respectively). In summary, of the 14 persons tested using HLA A2 presented epitopes, 4 had detectable responses, whereas a total of 9 of 14 persons (including these 4) had detectable responses when screened with the more comprehensive method. Moreover, in 2 of 4 persons positive for an HLA A2 restricted response, this was not the dominant response.

In vitro Stimulation Reveals Additional Subdominant HCV-specific CTL in a Majority of Individuals Having failed to demonstrate A2-restricted responses in circulating PBMC, despite frequent recognition of other epitopes, experiments were carried out to determine whether additional HLA A2 restricted responses are present but below the limits of detection in direct assays on fresh cells. To address this question, PBMC from 9 of the study subjects were stimulated in vitro. The study subjects included 5 who had previously been shown to have no HLA A2 restricted responses by Elispot and tetramer analysis. PBMC were stimulated in vitro in the presence of IL-2 and HCV peptides over 8 to 9 days. Four different HLA A2 restricted HCV peptides, for which tetramers were available, were used for stimulation.

FIGS. 5A–H shows the results f a tetramer analysis before and after stimulation of PBMC with peptides representing HCV epitopes. In subject P14, only one of four tetramers (NS3 1073) tested positive directly ex vivo. After 9 days of stimulation with the four respective peptides, 3 of four tetramers tested positive, with frequencies up to 30% of CD8+ T cells. Results by tetramer analysis using unstimulated cells were identical to results with the Elispot assay, with the same 4 subjects having detectable responses (Table 5; representative example shown in FIGS. 5A–H).

TABLE 5

| SUBJECT | NS3 1073 | | NS4 1406 | | NS4 1851 | | NS5 2594 | |
|---|---|---|---|---|---|---|---|---|
| | Ex vivo | stim. | Ex vivo | stim. | Ex vivo | stim. | Ex vivo | stim. |
| P2 | 1.31 | 14% | 0.12% | 4% | <0.02 | <0.02 | <0.02 | 11% |
| P3 | <0.02 | <0.02 | <0.02 | <0.02 | <0.02 | <0.02 | <0.02 | <0.02 |
| P4 | <0.02 | 12% | <0.02 | 9% | <0.02 | <0.02 | <0.02 | <0.02 |
| P6 | 0.42% | 43% | 0.09% | 2.50% | <0.02 | <0.02 | 0.23% | 17% |
| P8 | <0.02 | 1.50% | <0.02 | <0.02 | <0.02 | <0.02 | <0.02 | <0.02 |

TABLE 5-continued

| | NS3 1073 | | NS4 1406 | | NS4 1851 | | NS5 2594 | |
|---|---|---|---|---|---|---|---|---|
| SUBJECT | Ex vivo | stim. | Ex vivo | stim. | Ex vivo | stim. | Ex vivo | stim. |
| P10 | <0.02 | 0.40% | <0.02 | 41% | <0.02 | <0.02 | <0.02 | <0.02 |
| P11 | <0.02 | 2% | <0.02 | 5.60% | <0.02 | <0.02 | 0.23% | 25% |
| P12 | <0.02 | <0.02 | <0.02 | <0.02 | <0.02 | <0.02 | <0.02 | <0.02 |
| P14 | 0.17% | 31% | <0.02 | 6.60% | <0.02 | <0.02 | <0.02 | 2.50% |
| Total positive | 3/9 | 7/9 | 2/9 | 6/9 | 0/9 | 0/9 | 2/9 | 4/9 |

Boldface indicates strongly positive result.

Boldface Indicates Strongly Positive Result

After stimulation, responses to additional epitopes, which had been below the limits of detection in the direct assays were present using this technique. In the 4 subjects who had detectable responses to HLA A2 epitopes in the direct ex vivo assay, 3 had additional responses that first became detectable after in vitro expansion (Table 5). For the one individual in whom no additional response was detected (P6), the three ex vivo detectable responses were readily expanded. Of the five subjects tested with negative results directly ex vivo, three (P4, P8 and P10) tested positive after specific stimulation. One epitope (NS4 1851–1859) was never detected, either directly ex vivo or after stimulation. These results show that memory responses to HCV peptides are present in the majority of infected persons, but that HLA A2-restricted responses are often weak and are usually not the dominant responses in persons with HCV infection.

Identification of Viral CTL Epitopes

The comprehensive analysis of HCV-specific CD8+ T lymphocytes described herein indicate that CTL responses are reliably detected directly ex vivo in the majority of anti-HCV positive individuals, without requiring predictive algorithms or prior knowledge of HLA type. Using 301 overlapping peptides spanning all HCV proteins, circulating HCV-specific CD8+ T-cells were detected in 9/14 subjects tested, whereas only 4 of these HLA A2 positive persons had detectable HLA A2 restricted responses without prior in vitro stimulation. Importantly, half of the responses detected were directed against previously uncharacterized epitopes, and the vast majority of previously reported A2 epitopes were either not targeted or were below the limits of detection in persons with clear CD8+ T cell responses to other epitopes. These data indicate that HLA type does not predict dominant HCV responses in seropositive individuals, that targeted epitopes are scattered throughout all gene products, and that no epitopes or regions are preferentially targeted by the majority of infected persons.

Earlier methods were limited because of their reliance on HLA-A2 restricted epitopes. For example, since HLA A2 is less frequently expressed exposed in non-Caucasian populations, the data from earlier studies is not applicable to diverse, e.g., not predominantly Caucasian, populations. The data described herein indicates that the analysis of responses restricted by a single HLA allele cannot be used as a surrogate marker for the overall HCV-specific CTL response. A response to any of the 19 previously described HLA A2-restricted HCV epitopes was seen in only 4/14 subjects, yet 9 of 14 had responses when the comprehensive approach using overlapping peptides was applied. In those HLA A2 positive persons with HLA A2-restricted responses, the previously identified epitopes were not always the dominant responses. In vitro simulation increased the detection of responses to some A2 restricted epitopes, indicating that weak responses were present but underscoring that these responses were minor compared to those directed at non-HLA A2 epitopes in a number of persons.

The assays described herein permit assessment of the relative predictive ability of algorithms designed to predict CTL epitopes, using the more sensitive techniques of Elispot and tetramer analysis. The results showed that a minority of predicted HLA A2 restricted epitopes are detected directly in PBMC. Of the 19 HLA A2 restricted HCV-specific epitopes presently described, only 3/19 (NS3 1073, NS3 1406, NS5B 2594) were recognized by Elispot analysis in any of the patients, and these 3 were repeatedly detected in more than one person. These findings were confirmed by tetramer analysis to exclude the possibility of specific cells being present, but undetected due to a defects in functional properties. While frequencies of HCV-specific cells were indeed higher when analyzed by tetramer analysis the results by Elispot correlated significantly in their relative frequency. Tetramer analysis did not reveal any response not detected by the Elispot assay. Responses were detected in individuals infected with various genotypes, despite our peptides being derived from a genotype 1 sequence. For one of the epitopes (NS3 1073) cross reactivity with a flu epitope may be a mechanism leading to preferred recognition.

Using the peptide matrix approach, circulating HCV-specific CTL responses were detected in 6/10 individuals with chronic HCV infection. The detection is comparable to results obtained by cloning from liver derived lymphocytes where such a response was detected in 45% of subjects. The data suggest that, while the frequencies of HCV-specific cells have been shown to be higher in the liver, the matrix assay is able to detect HCV-specific CTL with similar sensitivity in the periphery without the need of in vitro expansion.

Mapping HCV CTL Epitopes

The detailed analysis of the HCV-specific CD8+ T cell response requires a comprehensive screening that cannot be substituted by testing a limited number of epitopes as indicators of the T-cell response. The study of HCV-specific CTL directly ex vivo without the restriction to certain HLA alleles is important in determining the role of CD8+ T cells in control and immunpathology of HCV infection. The data indicate that the response is more limited than expected.

Four optimized nominal HCV epitopes were defined and are shown in Table 6.

TABLE 6

| HCV PROTEIN | POSITION | SEQUENCE | HLA RESTRICTION | SUBJECT |
|---|---|---|---|---|
| E2 | 610–618 | DYPYRLWHY (SEQ ID NO: 42) | Cw7 | P4 |
| NS3 | 1435–1443 | ATDAL MTGY (SEQ ID NO: 45) | A1 | P2 |
| NS5B | 2568–2577 | QPEKGGRKPA (SEQ ID NO: 47) | B55 | P7 |
| NS5B | 2898–2907 | SPGEINRVAA (SEQ ID NO: 48) | B55 | P7 |

Resolved and Persistent Hepatitis C Virus Infection: CD8+ T Cell Responses Differ in Breadth and Magnitude, but not in Their Phenotype or Function Vigorous HCV-specific CD8+ T-cell responses have been reported during acute HCV infection, but the long-term fate of these responses remains ill-defined. A comprehensive comparative assessment of HCV specific CD8+ T cell responses was performed in individuals with both persistent and resolved infection. Responses were identified using a matrix of HCV peptides spanning the entire HCV genome in an ELISpot assay. The phenotype of these responses was determined using a panel of HCV tetramers that were tailored to match both the individuals HLA type and the epitopes identified in the screening ELISpot assay. The functional capacity of these cells was assessed. Responses in individuals with resolved infection were significantly more common, targeted more epitopes and were stronger compared to individuals with persistent infection. They were also more broadly directed and could be detected years after HCV resolution. In both cohorts, responses were directed against a range of HCV peptides. Surprisingly, HCV specific CD8+ T-cells exhibited uniformly an early memory phenotype in or without the presence of persistent viraemia. In addition, HCV specific responses were functionally intact in that they expanded in vitro following a single round of peptide stimulation and produced IFN-γ in an 18 hour ELISpot assay. The results indicated that CD8+ T cell responses in individuals with resolved infection differ in breadth and magnitude, but not in their phenotype or function. This indicates that broadening and strengthening of the HCV-specific CTL response is a clinically beneficial strategy for the development of HCV vaccines and immunotherapeutic interventions.

Studies were carried out to test the hypothesis that spontaneous control of HCV infection is associated with persistent HCV-specific CD8+ T cell responses. CD8+ T cell responses in 20 individuals following spontaneous resolution of HCV infection were comprehensively analyzed and compared these to the responses observed in 20 individuals with persistent infection. In contrast to previous studies, CD8+ T cell responses were analyzed by targeting the entire HCV polypepetide, using ex vivo ELISpot assays in addition to an unprecedented number of HCV tetramers. This strategy permitted a determination of the HCV-response directed against all HCV proteins irrespective of HLA type. The evaluation was carried out as follows.

Study Subjects

Twenty subjects (subjects R1 to R20) with spontaneously resolved HCV infection, defined as the absence of detectable HCV RNA by PCR (HCV Roche Amplicor assay, detection limit of 300 HCV RNA copies/ml of plasma) in the presence of HCV antibodies (third generation EIA) on at least two consecutive occasions were studied. Additionally, twenty treatment naïve patients with chronic HCV infection were consecutively enrolled from the outpatient clinic. All subjects were studied at least 2 years after acute HCV infection. Further subject characteristics are listed in Table 7.

Strategy for Defining CD8+ T Cell Responses

T cell responses were comprehensively identified in each patient in an Enzyme Linked Immuno-Spot (ELISpot) assay for IFN-γ, using 301 peptides (20mers overlapping by 10 AA) spanning the entire HCV genome in addition to a panel of previously defined HCV epitopes (n=83). In order to define the optimal peptide sequence for novel HCV epitopes identified in the screening ELISpot assay, a series of peptide truncations was generated. Peptide stimulated CD8+ T-cell lines were generated to confirm both restriction and specificity as well as to assess the proliferative capacity of the antigen specific T cells. In addition a panel of tetramers, both new patient specific epitopes (defined in the aforementioned ELISpot assay) and previously defined epitopes were used to quantify and phenotype antigen specific CD8+ T cells, independent of function.

Synthesis of HCV-derived Peptides

Peptides corresponding to the amino acid sequence of the HCV-1a strain, spanning the entire HCV polypeptide, were synthesized as free acids using a standard 9-fluorenyl-methoxy carbonyl method. The 301 peptides, used in the initial screening assay were 20 amino acids in length, overlapping adjacent peptides by 10 amino acids. The 83 optimal epitope peptides were 8 to 10 amino acids in length. Additional truncated peptides were synthesized to determine the optimal epitope sequence.

HLA Typing

HLA typing was using standard serological and molecular techniques.

ELISpot Assay 96-well polyvinylidene plates (Millipore) were coated with 2.5 mg/ml recombinant human anti-IFN-γ antibody (Endogen) in PBS at 4° C. overnight. Fresh or previously frozen PBMC were added at 200,000 cells/well in 140 ml R10 medium (RPMI 1640 [Sigma-Aldrich], 10% FCS [Sigma-Aldrich], and 10 mM Hepes buffer [Sigma-Aldrich] with 2 mM glutamine and antibiotics [50 U/ml penicillin-streptomycin]). Peptides were added directly to the wells at a final concentration of 10 mg/ml. The plates were incubated for 18 hours at 37° C., 5% $CO_2$. Plates were then washed, labeled with 0.25 mg/ml biotin-labeled anti-IFN-γ (Endogen), and developed by incubation with streptavidin-alkaline phophatase (Bio-Rad) followed by incubation with BCIP/NBT (Bio-Rad) in Tris-buffer (pH 9.5). The reaction was stopped by washing with tap water and the plates were dried, prior to counting on an ELISpot reader (AID, Strassberg, Germany). For quantitation of ex vivo responses, the assay was performed at least in duplicate and background was not more than 15 spot-forming cells (SFC)/$10^6$ PBMC. Responses were considered positive if the number of spots per well minus the background was at least 25 SFC/$10^6$ PBMC. Phytohemagglutini (PHA) served as a positive control.

HLA Class I-peptide Tetramer Staining

HLA class I-peptide tetramers were prepared using standard methods (e.g., the method described by Lechner et al., 2000, J Exp Med 191:1499–15126), and included tetramers specific for 4 epitopes restricted by HLA-A2, one epitope restricted by HLA A1, HLA A24 and HLA B35, respectively:

HLA A2: NS3 peptide 1073–1081, CINGVWCTV (SEQ ID NO: 8);

NS4 peptide 1406–1415, KLVALGINAV (SEQ ID NO: 11);
NS4 peptide 1987–1995 VLDSFKTWL (SEQ ID NO: 75);
NS5B peptide 2594–2603, ALYDVVTKL(SEQ ID NO: 18);
HLA A1: NS3 peptide 1435–1443 ATDALMTGY(SEQ ID NO: 45);
HLA A24: NS4 1745–1754 VIAPAVQTNW(SEQ ID NO: 72);
HLA B35: NS3 1359–1367 HPNIEEVAL(SEQ ID NO: 70).

One half to 1 million PBMC were stained. Tetramer staining was performed for 20 minutes at 37° C. After washing for 5 minutes with PBS containing 1% FCS at room temperature (RT), cells were pelleted and directly stained with combinations of the following antibodies: CD8-PerCP, CD27 FITC, CD28 APC, and CD45RA FITC (all from Becton Dickenson). For indirect antibody staining using CCR7, staining was performed as follows. After 2 consecutive washes (as above) cells were pelleted and stained with anti CCR7-Ab for 30 minutes at room temperature. After two further washes, cells were pelleted again and a secondary anti-mouse-IgM-APC-conjugated Ab (Caltag) was added for 30 minutes at RT. Cells were washed twice and directly conjugated CD8-PerCP Ab was added for 20 minutes at 4° C. to the cell pellets. All staining was performed in a volume of 100 µl PBS in the presence of 10 µl goat immunoglobulin to prevent non-specific Ab binding. Flow cytometric analysis was performed with a Becton Dickinson fluorescence-activated cell sorter (FACS) Calibur, and data analysis was performed using the CellQuest software. Staining was considered positive if tetramer-positive cells formed a cluster distinct from the tetramer negative CD8+ T cell population and the frequency of tetramer positive cells was greater than 0.02% of the total CD8+ population.

Intracellular IFN-γ Staining

Intracellular cytokine staining (ICS) IFN-γ was performed using standard methods, (e.g., as described in Lauer et al., 2002. J Virol 76:6104–6113). $1\times10^6$ PBMC were incubated with 4 µM peptide and anti-CD28 and anti-CD49d MAbs (1 µg/ml each; Becton Dickinson) at 37° C. and 5% $CO_2$ for 1 h before the addition of Brefeldin A (1 µl/ml; Sigma-Aldrich). The cells were incubated for an additional 5 h at 37° C. and 5% CO2. PBMC were then washed and stained with surface antibodies, antigen-presenting cell-conjugated anti-CD3 and phycoerythrin-conjugated anti-CD8 (Becton Dickinson) at RT for 20 min. following the washing, the PBMC were fixed and permeabilised (Caltag, Burlingame, Calif.), and the fluorescein isothiocyanate-conjugated anti-IFN-γ MAb (Becton Dickinson) was added. Cells were then washed and analyzed on a FACS-Calibur flow cytometer using CELLQuest software (Becton Dickinson).

Bulk Stimulation of Peripheral Blood Mononuclear Cells

In order to establish CD8+ T cell lines, cryopreserved or fresh PBMC ($4-10\times10^6$) were stimulated with 1 µg/ml of synthetic HCV peptide and 0.5 mg/ml of the costimulatory antibodies anti-CD28 and anti-CD49d (Becton Dickinson) in R10. Irradiated feeder cells ($20\times10^6$ allogeneic PBMC) were added to the culture in a 25-cm2 culture flask (Costar, Cambridge, Mass.). Recombinant interleukin-2 (IL-2, 25 IU/ml) was added on day 2 and twice a week thereafter.

Cytotoxicity Assay

Autologous B lymphocyte cell lines (B-LCL) were pulsed with 10 µg of peptide and $[^{51}Cr]O_4$ (New England Nuclear, Boston, Mass.), and incubated for one hour at 37° C. in 5% $CO_2$. The B-LCL target cells were washed three times with cold R-10 medium and incubated with effector cells at 37° C. for 4 h in three replicate wells. Cellular release of $[^{51}Cr]O4$ into the supernatant was measured using a Top Count Microplate scintillation counter (Packard Instrument-Company, Meriden, Conn.), and the percent specific cytotoxicity was calculated by the formula % lysis=[(experimental release−spontaneous release)/(maximum release−spontaneous release)]×100. Results are reported as the mean of triplicate values. Only experiments with a spontaneous release of <20% were evaluated.

HLA Restriction

To define HLA restriction, partially HLA matched and mismatched heterologous BCL were pulsed with 10 µg of peptide for an hour, washed three times with R10 and then 2×105 of the BCL were added to the T-cell line instead of peptide. Cytotoxicity assays or ICS were then performed as described above.

Statistical Analysis

Statistical analysis (Mann-Whitney rank sum test and correlation coefficient) was performed using GraphPad Prism® 3.0a for Macintosh.

TABLE 7

| Patient ID | HLA | Peptides recognized by CD8+ T-cells | |
|---|---|---|---|
| R1 | A3, 66 B7, 49 Cw7 | E2-610 Cw7 YRLWHYPCTI (145) (SEQ ID NO: 59) | NS3-1070 ATCINGVCWTVYHGAGTRTI (860) (SEQ ID NO: 60) |
| R2 | A2, 3 B7, 60 Cw7 | Core-41 B7 GPRLGVRAT (110) (SEQ ID NO: 28) | E2-610 Cw7 YRLWHYPCTI (860) (SEQ ID NO: 61) |
| R3 | A2, 25 B37, 44 Cw7, 12 | NS2-831 A25 LSPYYKRYIS (475) (SEQ ID NO: 62) | NS2-957 B37 RDWAHNGL (900) (SEQ ID NO: 32) |
| | | NS3-1073 A2 CINGVCWTV (750) (SEQ ID NO: 63) | NS4-1758 A25 ETFWAKHMW (200) (SEQ ID NO: 64) |
| | | NS4-1966 B37 SECCTPCSGSW (850) (SEQ ID NO: 65) | NS5-2225 A25 ELIEANLLW (210) (SEQ ID NO: 66) |
| | | NS5-2594 A2 ALYDVVTKL (750) (SEQ ID NO: 18) | NS5-2819 A25 TARHTPVNSW (750) (SEQ ID NO: 67) |
| R4 | A2, 29 B44 Cw16 | Core-88 B44 NEGCGWMGW (510) (SEQ ID NO: 68) | |
| R5 | A24, 33 B35, 65 Cw4, 8 | E1-207 B35 CPNSSIVY (500) (SEQ ID NO: 69) | NS3-1359 B35 HPNIEEVAL (195) (SEQ ID NO: 70) |
| | | NS4-1695 B35 IPDREVLY (160) (SEQ ID NO: 71) | NS4-1745 A24 VIAPAVQTNW (705) (SEQ ID NO: 72) |
| | | NS5-2162 B35 EPEPDVAVL (25) (SEQ ID NO: 73) | NS5-2912 (B57) LGVPPLRAWR (150) (SEQ ID NO: 74) |

TABLE 7-continued

| Patient ID | HLA | Peptides recognized by CD8+ T-cells | |
|---|---|---|---|
| R6 | A11, 29 B35, 40 Cw3, 4 | neg | |
| R7 | A1 B8, 49 Cw7 | neg | |
| R8 | A2, 24 B15, 44 Cw3, 7 | NS4-1987 A2 VLDSFKTWL (65) (SEQ ID NO: 75) | NS5-2461 TSRSACQRQKKVTFDRLQVL (45) (SEQ ID NO: 76) |
| R9 | A1, 68 B53, 57 Cw4, 6 | E2-541 B57 NTRPPLGNWFG (90) (SEQ ID NO: 77) NS3-1435 A1 ATDALMTGY (225) (SEQ ID NO: 45) NS5-2912 B57 LGVPPLRAWR (350) (SEQ ID NO: 79) | NS3-1175 A68 HAVGLFRAA (290) (SEQ ID NO: 78) NS5-2629 B57 KSKKTPMGF (125) (SEQ ID NO: 36) |
| R10 | A1, 2 B57, 63 | NS3-1406 A2 KLVALGINAV (60) (SEQ ID NO: 11) | NS3-1801 B57 LTTSQTLLF (50) (SEQ ID NO: 80) |
| R11 | A1, 11 B8, 44 Cw7, 16 | NS3-1395 B8 HSKKKCDEL (120) (SEQ ID NO: 30) | |
| R12 | A1, 11 B35, 57 Cw4, 6 | NS3-1435 A1 ATDALMTGY (75) (SEQ ID NO: 45) | |
| R13 | A1, 11 B8, 65(14) Cw7, 8 | NS3-1435 A1 ATDALMTGY (45) (SEQ ID NO: 45) | NS5-2912 LGVPPLRAWR (65) (SEQ ID NO: 81) |
| R14 | A2, 11 B65(14), 57 Cw6, 8 | E2-541 B57 NTRPPLGNWFG (60) (SEQ ID NO: 82) NS3-1751 VFTGLTHIDAHFLSQTKQSG (75) (SEQ ID NO: 84) NS3-1801 LTTSQTLLFNILGGWVAAQL (65) (SEQ ID NO: 86) | NS2-941 LGALTGTYVYNHLTPLRDWA (60) (SEQ ID NO: 83) NS3-1771 GIQYLAGLSTLPGNPAIASL (45) (SEQ ID NO: 85) |
| R15 | A1, 11 B37, 62(15) Cw4, 6 | neg | |
| R16 | A2, 23 B7, 44 Cw4, 7 | Core-41 B7 GPRLGVRAT (130) (SEQ ID NO: 28) | NS3-1406 A2 KLVALGINAV (30) (SEQ ID NO: 11) |
| R17 | A2, 3 B41, 44 Cw5, 17 | NS3-1406 A2 KLVALGINAV (90) (SEQ ID NO: 11) | |
| R18 | A24, 33 B7, 65(14) Cw7, 8 | NS3-1610 CLIRLKPTLHGPTPLLYR (100) (SEQ ID NO: 87) | |
| R19 | A3, 24 B7, 37 Cw6, 7 | Core-111 B7 DPRRRSRNL (155) (SEQ ID NO: 29) | E1-322 MMMNWSPTT (70) (SEQ ID NO: 88) |
| R20 | A2 B44, 57 Cw5, 6 | NS3-1406 A2 KLVALGINAV (60) (SEQ ID NO: 11) | NS5-2594 A2 ALYDVVTKL (65) (SEQ ID NO: 18) |

The peptides are described by the HCV-protein together with the aa position in the HCV-H77 sequence, followed by the HLA restriction of the peptide if known (HLA sequence in brackets means that the described HLA sequence is not present in the respective subject) and the peptide sequence. The numbers inbrackets indicate the strength of the respective response in the ELISpot assay (in SFC/$10^6$ PBMC).

TABLE 8

| Patient ID | HLA | HCV GENOTYPE | HCV RNA (IU/ml) | ALT (IU/ml) | Peptides recognized by CD8+ T-cells | |
|---|---|---|---|---|---|---|
| C1 | A1, 68 B14, 55 Cw7 | 1b | 300800 | 216 | NS5-2568 B55 QPEKGGRKPA (65) (SEQ ID NO: 47) | NS5-2898 B55 SPGEINRVAA (65) (SEQ ID NO: 48) |
| C2 | A1, 2 B37, 44 Cw5, 6 | 2a/2c | 38600 | 21 | NS2-957 B37 RDWAHNGL (90) (SEQ ID NO: 32) NS3-1406 A2 KLVALGINAV (50) (SEQ ID NO: 11) | NS3-1073 A2 CINGVCWTV (120) (SEQ ID NO: 8) NS5-2594 A2 ALYDVVTKL (70) (SEQ ID NO: 18) |
| C3 | A3, 30 B13, 51 Cw6, 15 | 1a | 530000 | 32 | NEG | |
| C4 | A1, 2 B8, 55 Cw3, 7 | 1a | 18400 | 43 | NS3-1435 A1 ATDALMTGY (85) (SEQ ID NO: 45) NS5-2898 B55 SPGEINRVAA (45) (SEQ ID NO: 48) | NS5-2568 B55 QPEKGGRKPA (40) (SEQ ID NO: 47) |
| C5 | A2, 29 B18, 40 Cw3, 5 | 2b | 456490 | 338 | NEG | |
| C6 | A1, 31 B8 Cw7 | 2b | 220970 | 274 | NEG | |
| C7 | A1 B15 Cw9, 10 | 1a | 342980 | 29 | NEG | |
| C8 | A2, 3 B39, 44 Cw7, 16 | 2b | 7840000 | 205 | P7-790 Cw7 FYGMWPLL (70) (SEQ ID NO: 89) | NS3-1171 (A68) HCPAGHAVGIFRAAVCTRGVA (60) (SEQ ID NO: 90) |
| C9 | A1 B8 Cw7 | 1b | 428540 | 58 | NS2-831 LSPYYKRYISWCLWWLQYFL (135) (SEQ ID NO: 91) | |
| C10 | A1, 26 B44, 51 Cw4, 14 | 3a | >1000000 | 92 | Neg | |
| C11 | A11, 23 B35, 44 Cw4 | 1b | 12480000 | 106 | Neg | |
| C12 | A2, 3 B7, 44 Cw7 | 1b | 203000 | 47 | Neg | |
| C13 | A2, 26 B35, 38 Cw4, 12 | 1a | 9760000 | 152 | NS2-871 DAVILLMCAVHPTLVFDITK (130) (SEQ ID NO: 92) | |

TABLE 8-continued

| Patient ID | HLA | HCV GENOTYPE | HCV RNA (IU/ml) | ALT (IU/ml) | Peptides recognized by CD8+ T-cells | |
|---|---|---|---|---|---|---|
| C14 | A2, 36 B52, 65 Cw8, 15 | 1a | 5340000 | 48 | Neg | |
| C15 | A2, 11 B35, 44 Cw7, 9 | 2a/c | 5240000 | 68 | Neg | |
| C16 | A23, 30 B7, 52 Cw7, 16 | 1a | >1000000 | 120 | Neg | |
| C17 | A3, 32 B7, 14 Cw7, 8 | 1a | 152000 | 96 | E2-610 Cw7 YRLWHYPCTI (75) (SEQ ID NO: 93) NS4-1941 (B38) AARVTAIL (255) (SEQ ID NO: 95) | NS4-1744 (A25) EVIAPAVQTNW (70) (SEQ ID NO: 94) |
| C18 | A2, 29 B44, 50 Cw4, 16 | 3a | 1213300 | 100 | P7-790 A29 FYGMWPLLL(280) (SEQ ID NO: 96) | NS5-2594 A2 ALYDVVTKL (70) (SEQ ID NO: 18) |
| C19 | A1, 2 B8, 44 Cw1 | 1a | 796000 | 86 | NS5-2197 SVASSSASQLSA (120) | |
| C20 | A3, 24 B7, 35 Cw4, 7 | 1b | >850000 | 100 | neg | |

The peptides are described by the HCV-protein together with the aa position in the HCV-H77 sequence, followed by the HLA restriction of the peptide if known (HLA sequence in brackets means that the described HLA sequence is not present in the respective subject) and the peptide sequence. The numbers in brackets indicate the strength of the respective response in the ELISpot assay (in SFC/$10^6$ PBMC).

HCV-specific CD8+ T-lymphocytes can be Detected Directly ex vivo Years After Spontaneous Resolution of HCV Infection Studies were carried out to determine whether spontaneous elimination of HCV infection is associated with a long-lasting broad and vigorous immune response by CD8+ HCV-specific T-cells. A cohort of individuals who had cleared HCV spontaneously at least 2 years prior to study entry (as indicated by a positive HCV antibody test and consistently negative HCV RNA) was assembled.

In previous studies using direct ex vivo techniques and selected HCV epitopes, only a few relatively weak responses were detected in persons who had spontaneously cleared HCV infection. In contrast, using this more comprehensive approach (FIGS. 6A–E) HCV-specific CD8+ T cell responses were detected in the vast majority of such patients (17/20, Table 7). In addition, the response detected was often multispecific and vigorous. Up to 8 epitopes were targeted in a single individual and the strength of some responses reached 900 SFC/$10^6$ PBMC in the ELISpot assay (Table 7) or 2.8% of CD8+ T cells in the ex vivo tetramer assay (FIG. 7A; patient R3). Many responses were directed against previously undescribed epitopes. Novel responses were confirmed to be mediated by CD8+ T cells, to have cytolytic activity and to have proliferative capacity as shown by expansion of specific cells after peptide stimulation (FIGS. 6A–E and and FIGS. 8A–L). The HLA restriction for 10 novel HCV epitopes (Table 9) were determined and finemapped.

TABLE 9

| HCV PROTEIN | AMINO ACID POSITION | SEQUENCE | HLA RESTRICTION | SEQ ID NO: |
|---|---|---|---|---|
| E1 | 207–214 | CPNSSIVY | B35 | 49 |
| E2 | 541–550 | NTRPPLGNWF | B57 | 50 |
| P7 | 790–798 | FYGMWPLLL | A29 | 51 |
| P7 | 790–797 | FYGMWPLL | Cw7 | 52 |
| NS3 | 1175–1184 | HAVGLFRAA | A68 | 53 |
| NS3 | 1801–1809 | LTTSQTLLF | B57 | 54 |
| NS4 | 1695–1712 | IPDREVLY | B35 | 55 |
| NS4 | 1745–1754 | VIAPAVQTNW | A24 | 56 |
| NS5 | 2162–2170 | EPEPDVAVL | B35 | 57 |
| NS5 | 2912–2921 | LGVPPLRAWR | B57 | 58 |

Figure 9A:
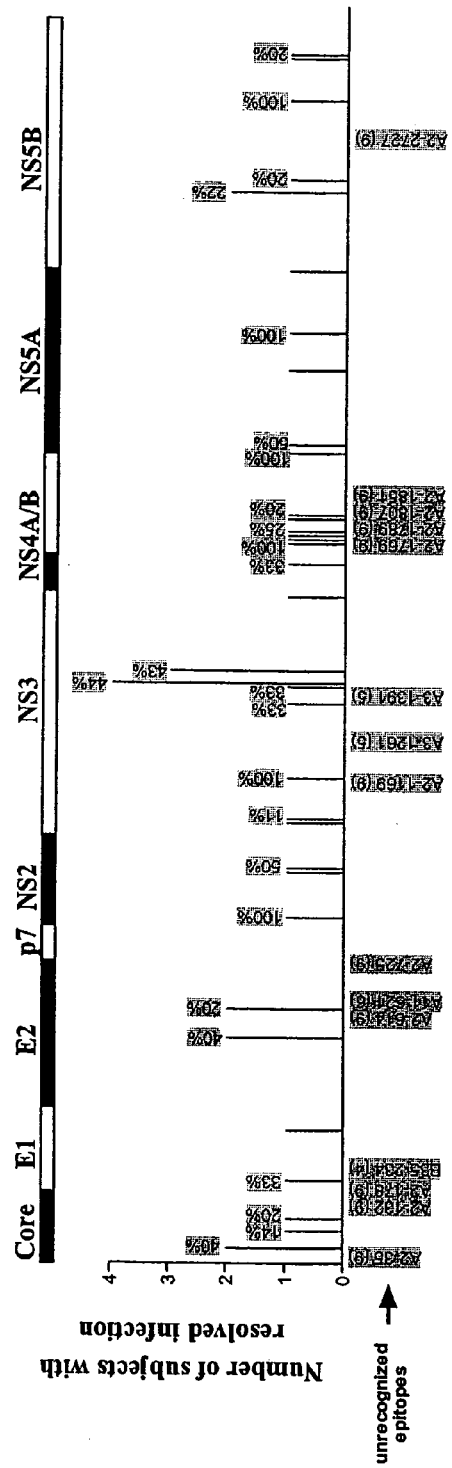
FIGS. 9A–B are bar graphs showing a distribution of HCV epitopes and frequency of recognition. Targeted epitopes within the HCV genome (corresponding to the given HCV genome map above) are shown for individuals with resolved (FIG. 9A) and chronic (FIG. 9B) infection. Each bar represents a distinct epitope and the number of subjects targeting each epitope is indicated through the length of the bar. The % above each bar gives the proportion of individuals responding to that epitope/total number of individuals with the same HLA restriction for that epitope (in cases where the HLA restriction of the response is known). Previously described HLA restriction elements targeting HCV epitopes (corresponding to the position in the genome map above) that were not recognized in this study by any subject is given below the y axis. The number of subjects in this study with that HLA restriction is given in parenthesis.
Figure 9B:
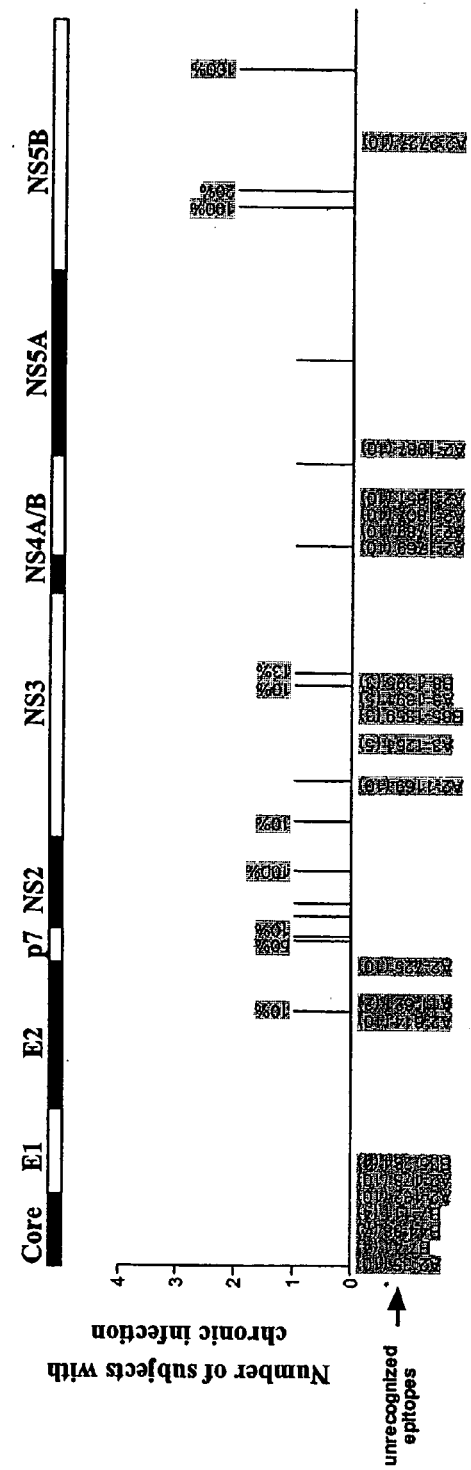

Overall, the HCV-specific CD8+ T cell responses were broadly distributed over the whole HCV genome (FIG. 4). Whilst some responses were targeted by several individuals, few of the HCV epitopes were immunodominant (FIGS. 9A–B). Some of previously described HCV epitopes were not recognized by any individual, despite the fact that certain HLA alleles were present in up to 9 subjects of the cohort. These results demonstrate the persistence of a highly diverse HCV-specific CD8+ T-cell response in the absence of detectable viremia.

Figure 10A:
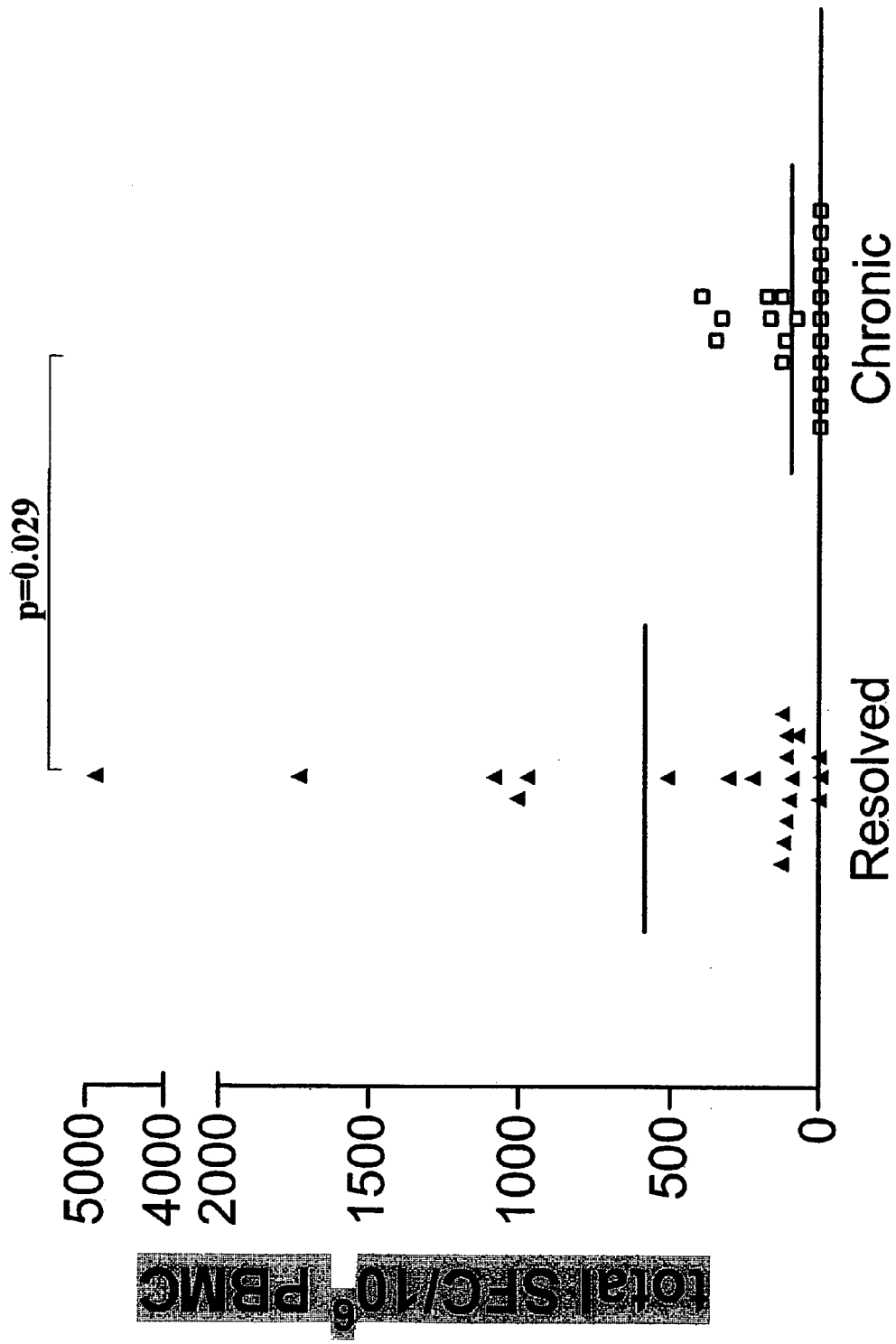
FIGS. 10A–B are scatter plot diagrams showing comparisons of the strength and breadth of the HCV-specific CD8+ T-cell response. In each individual, the summation of spot-forming cells (SFC) for all epitopes targeted by that individual (FIG. 10A), the number of epitopes targeted by each individual (FIG. 10B). Open squares and closed triangles represent individuals with chronic and resolved infection, respectively.
Figure 10B:
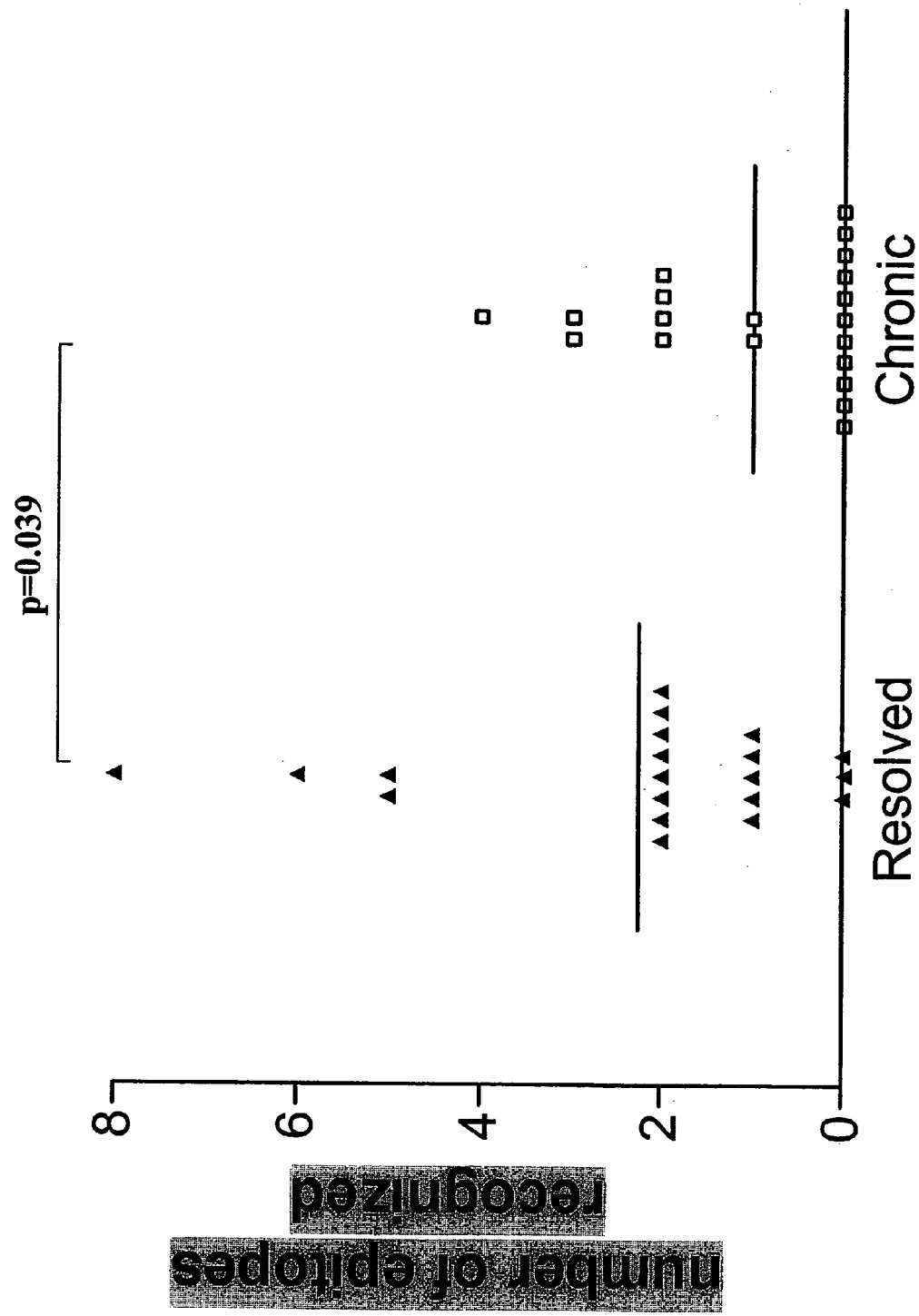
Figure 11M:
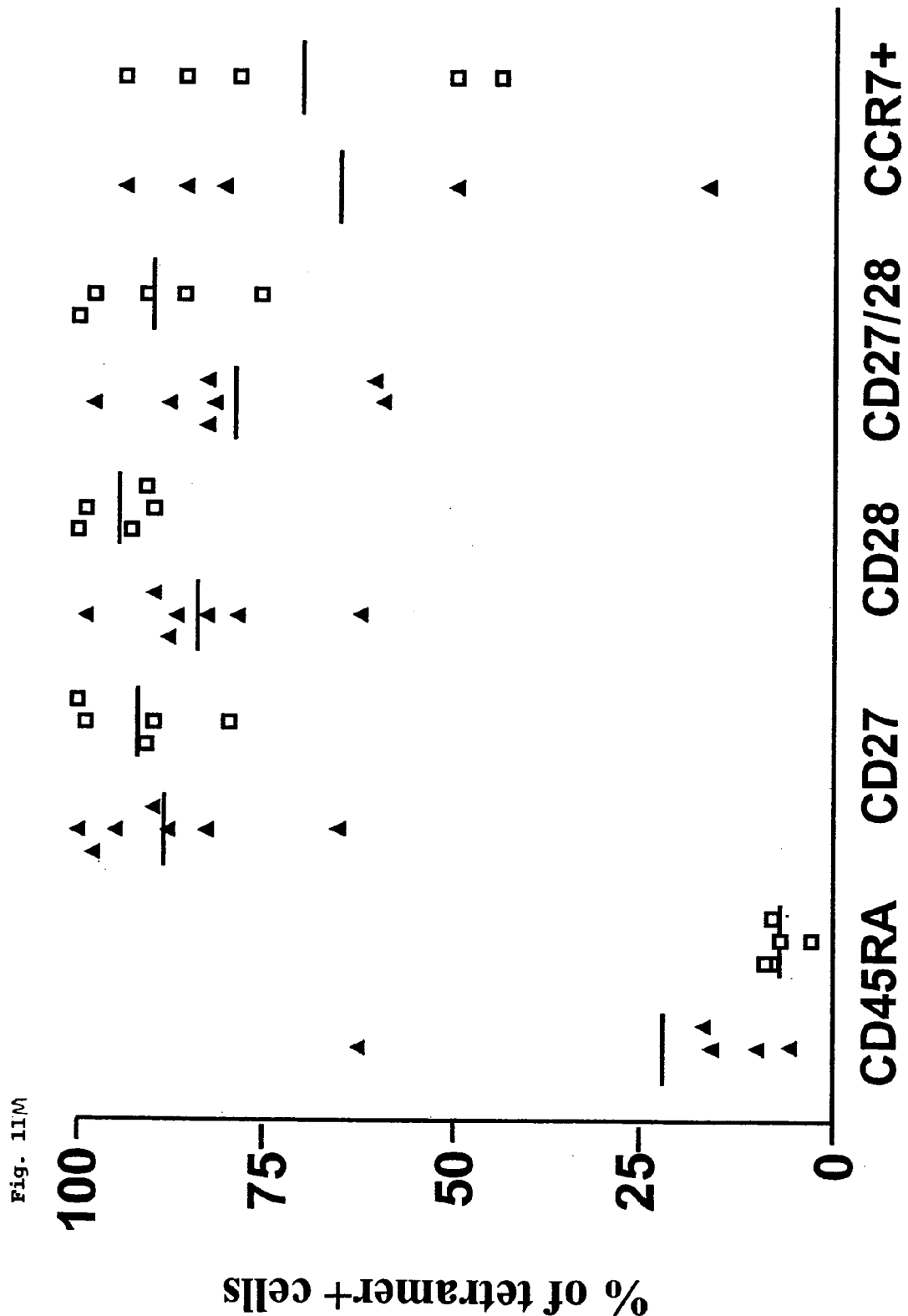
FIG. 11M is a scatter plot diagram showing an analysis of phenotypic marker expression across all tetramer responses analyzable. Open squares and closed triangles represent individuals with chronic and resolved infection, respectively. There were no significant differences between the two groups.

HCV-specific CD8+ T-lymphocytes are Detected Less Commonly and with Lower Frequencies in Individuals with Chronic HCV Infection As previous studies generated conflicting results when comparing individuals with resolved and chronic infection, a comprehensive assay was applied to a similar cohort with chronic untreated HCV infection. This cohort did not significantly differ in its age and gender distribution. HCV genotype was also determined (Table 8). As expected there was a dominance of HCV genotype I in this cohort, as previously described for the U.S.A. and U.K. population. In contrast to subjects with resolved infection, a significantly smaller number of individuals with chronic disease had HCV-specific CD8+ T cell responses (Table 8, 9/20 vs 17/20, p=0.019). In addition their responses were generally weaker, i.e. lower in overall magnitude (mean 95 (0–400) vs 584 (0–4885) total SFC/$10^6$ PBMC, p=0.027, FIG. 10A) and narrower, i.e., directed against a smaller number of epitopes (mean 1 (0–4) vs 2.3 (0–8) epitopes targeted, p=0.039, FIG. 10B). However, it has also to be noted that there was a significant overlap between the two cohorts in terms of the breadth and the overall strength of the individual's response. As for the resolved individuals, the responses were directed against a range of HCV proteins, restricted by a variety of HLA alleles and were highly heterogeneous between individuals, with a lack of immunodominance (FIGS. 9A–B).

There was a lack of responses directed against core and E1 in the chronic cohort, but this difference was not statistically significant (p=0.165, Fisher's exact test).

The distribution of the major HLA alleles, for which most known HCV epitopes have been described, in the two cohorts was very similar (HLA A1 7 vs. 8, HLA A2 9 vs. 10, HLA A3 4 vs. 5, HLA A11 5 vs. 2, HLA B7 5 vs. 4, HLA B8 3 vs. 4, HLA B35 3 vs. 4 and HLA B44 7 vs. 8). Therefore a similar number of optimal epitopes matching the individual's HLA type have been tested in both groups, which is important as optimal epitope peptides are potentially more sensitive in the ELISpot assay.

This comprehensive direct ex vivo analysis in a large cohort of individuals with chronic HCV infection permitted a correlating the HCV-specific CD8+ T-cell responses with viral control and disease activity. Neither HCV viral load nor ALT values were significantly correlated with the overall strength of the HCV-specific CD8+ T-cell response ($r2=0.0145$, $p=0.61$ and $r2=0.0149$, $p=0.61$ respectively)

HCV-specific CD8+ T-lymphocytes do not Differ in their Phenotype and Functional Properties Between Chronic and Resolved Infection The results from the screening of HCV-specific CD8+ T cell responses in spontaneously resolved and chronically infected individuals was used to tailor additional assays using class I tetramers for 11 individuals for whom sufficient additional PBMC were available. The cells were tested for a set of markers associated with T-cell differentiation, e.g., CD45RA, CD27, CD28 and CCR7. As shown in FIGS. 11A–M, HCV-specific cells, with the exception of one epitope in an individual with resolved infection, typically displayed an "early memory" phenotype (double positive for CD27 and CD28, and low in CD45RA). CCR7 surface expression was relatively high, in accordance with an "early memory" phenotype.

Figure 12:
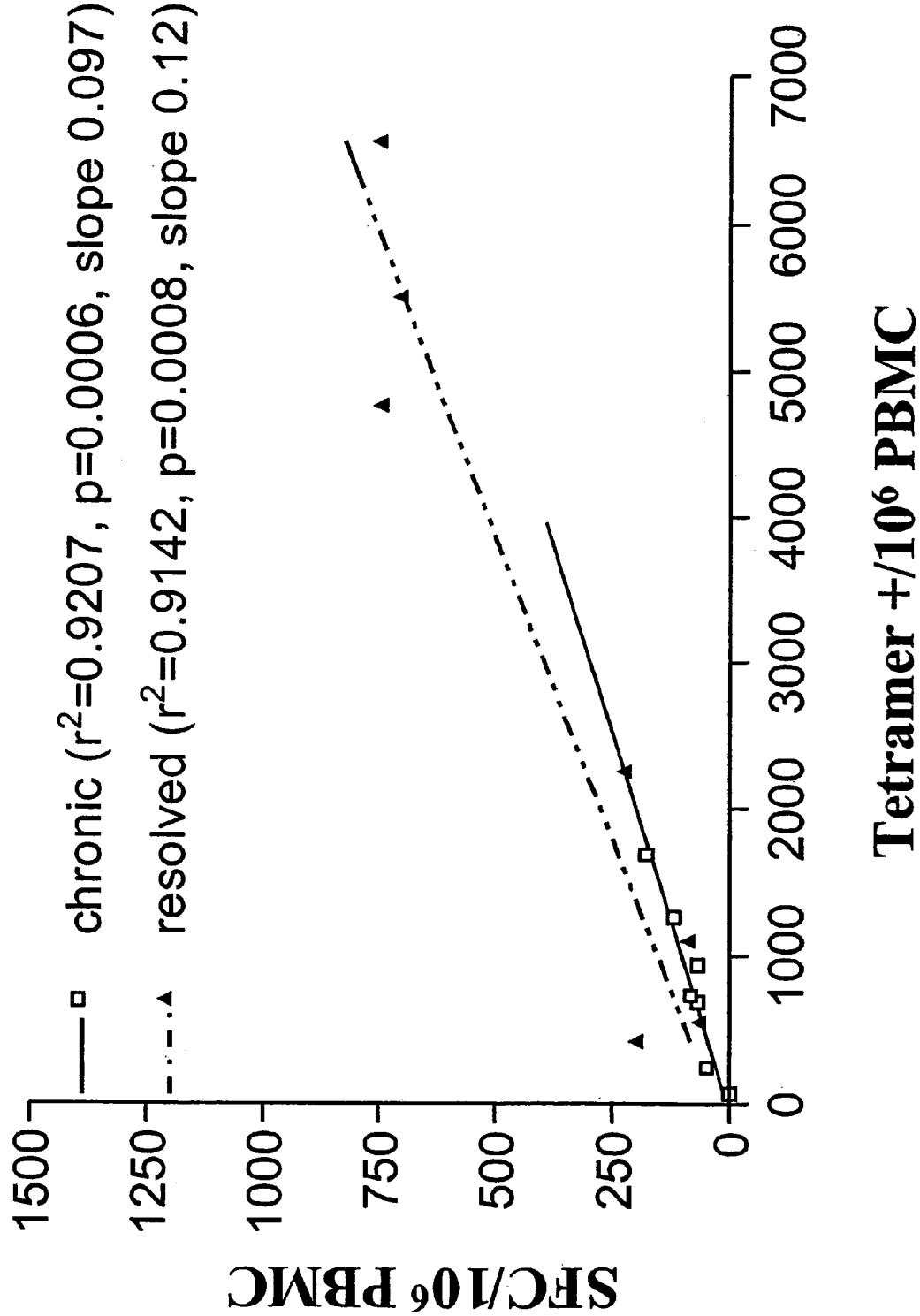
FIG. 12 is a line graph showing a plot of tetramer + T-cells and IFN-γ secretion. The number of tetramer positive cells was correlated with the number of IFN-γ producing specific cells as detected in the ELISpot assay ex vivo (SFC=spot forming cells). The number of IFN-γ secreting cells was universally lower, representing about 10% of tetramer positive cells in individuals with both resolved and chronic infection.

In addition, a correlated was made between the results from the functional IFN-γ ELISpot and the results of direct quantification by tetramer analysis. Only a minority of HCV-specific cells secreted IFN-γ, whether from individuals with resolved or chronic infection, a phenomenon referred to as a stunted phenotype (FIG. 12). By establishing peptide-specific T-cell lines (as shown in FIGS. 6A–E) used in ICS and cytoytoxicity assays, HCV-specific cells from subjects with chronic and with resolved infection were found to be able to proliferate in vitro and possess cytolytic function (FIGS. 6A–E).

Cytolytic T Cell Responses in Resolved and Persistent Hepatitis C Virus Infection The role of CD8+ T cells in the resolution of HCV remains controversial. This disclosure represents the first analysis, using peptides spanning the entire HCV viral genome to comprehensively map and compare CD8+ T cell responses in individuals with persistent and resolved HCV infection. This strategy has allowed a determination of the full breadth and the magnitude of the HCV specific T cell response in these patients irrespective of HLA type. Using tetramers specifically tailored to individual patients HCV specific T cell epitopes, the phenotype and function of CD8+ T cells in patients with chronic and resolved infection was assessed and compared.

The controversy surrounding the role of HCV specific CD8+ T cells has arisen through the limitations of the assays employed in earlier studies. It has been repeatedly demonstrated that CD8+ T are clearly detectable in vitro following several rounds of peptide stimulation in patients with chronic HCV infection. As new technologies such as tetramer and ELISpot technology developed, the detection of ex vivo CD8+ T cells responses became possible and it appeared that CD8+ T cell responses in chronic HCV infection were in fact relatively weak and difficult to detect. However these later studies were themselves limited by the use of techniques assessing only a small number of HCV specific epitopes. The present disclosure combines breadth and sensitivity and uses a variety of assays to assess the status of CD8+ T cell responses in individuals with resolved and persistent HCV infection. Further controversy surrounds the function of the antigen specific T cell response and the role of these cells in the resolution of HCV infection: some studies have suggested that CD8+ T cells are more easily detectable in patients with persistent HCV infection, compared to those with resolved infection—but are functionally impaired, whilst others reports have maintained that CD8+ T cell responses in patients with resolved infection are relatively robust.

Using the comprehensive approach described above, HCV-specific CD8+ T-cell responses were detected directly ex vivo in almost all individuals with resolved HCV infection. Up to 8 different epitopes were targeted in a single subject, with individual responses comprising up to 2.8% of CD8+ T-cells. In contrast, CD8+ T cells were detected in the minority of individuals with chronic infection, were typically weak and directed against only one or two epitopes. Overall, CD8+ T cell responses were significantly more common, more broadly directed, and of a greater magnitude in individuals with resolved HCV infection compared to those with persistent infection. The data indicated that broadening and strengthening the T cell repertoire in patients with persistent infection is clinically beneficial. Despite the significant differences between the two cohorts in the magnitude and breadth of the CD8+ T cell responses, the data indicated that at an individual level there is an overlap between the responses in individuals with persistent and resolved infection.

Recent studies have suggested that the expression of the costimulatory receptors CD27 and CD28 are associated with different stages of T cell differentiation (or maturation). Although the mechanism of T cell differentiation is not clearly defined it appears that CD8+ T cells may exist in a spectrum ranging from early differentiated (or central memory) cells high in CD27 and CD28, through to fully differentiated T cells low in CD27 and CD28 (or effector memory). Expression of CCR7, a secondary lymph node homing marker is associated with the early differentiated (central memory) phenotype. Functional differences between these phenotypes have also been observed. The early differentiated phenotype is generally associated with a high proliferative capacity, whilst the late differentiated phenotype is associated with the expression of cytotoxic factors such as perforin and granzyme A and cytotoxic functions. Furthermore it has been shown that enrichments of antigen specific T cells at different stages of differentiation occur and are virus specific.

HCV specific T cells in individuals with chronic infection have been described as distinct in that they appear at the immature end of the differentiation spectrum. If CD8+ T cell differentiation is subverted or diverted in HCV infection as a mechanism of evading host immunity, one would expect differences in the phenotype, (defined as the pattern of expression of CD28, CD27, CD45RA and CCR7) between individuals with resolved and persistent infection. The analysis of the phenotype of HCV specific CD8+ T cells employed 7 different tetramers based on 4 different HLA alleles. The phenotype of HCV specific CD8+ T cells was found to be CD27High, CD28High, CD45 RALow, and CCR7 High in each epitope in all individuals with both chronic and resolved infection—with the exception of a single response in one patient with resolved infection (FIGS. 11C, F I, L; patient R3 epitope NS5-2594), where responses to one of two phenotyped epitopes were CD27High, CD28High, CD45RAHigh and CCR7Low. The finding of relatively high CCR7 expression is consistent with the other markers of an early phenotype and extends previous more limited studies and contrasts with the findings in acute and early chronic disease. Distinct phenotypes, in two different epitopes restricted by the same HLA allele in the same individual was observed. Although the explanation for this is not clear it could relate to the avidity of the responses, which differ by 2 logs. Thus the relative amount of antigen "sensed" by the two T cell populations might differ quite considerably in vivo and contribute to their distinct evolution within one individual.

Whilst it is clear that distinct phenotypes may arise, the data suggests that the maturation phenotype in individuals with both resolved and chronic infection is relatively consistent. These finding are surprising, for although the phenotype observed is compatible with lack of recent antigen exposure and therefore predicted in the resolved group, the same phenotype is more difficult to account for in the presence of ongoing antigenic stimulation in patients with chronic infection. Furthermore, this phenotype is not seen in other persistent but controlled virus infections such as Cytomegalovirus. There are a number of possible mechanisms to account for the observed early memory phenotype. Firstly, the effector memory population may be compartmentalized to the liver where they actively contribute to the control of viraemia. Alternatively, these cells may be compartmentalized to the liver where they are deleted following interaction with antigen presented in the liver environment—a mechanism, which possibly contributes to viral persistence. Finally effector memory cells may not be generated and therefore will not be detected in the peripheral blood or the liver through mechanisms such as the infection and malfunction of dendritic cells in HCV infected individuals that might abnormally prime HCV specific CD8+ T cells. Analysis of the phenotype and function of intrahepatic HCV specific CD8+ T cells, and a clearer understanding of the mechanisms of T cell differentiation and the association with different viral specificities is required to clarify these mechanisms.

CD8+ T cell lines from individuals with both resolved and persistent infection were generated and have shown that that even weak responses, which are not detectable directly ex vivo, can be readily expanded in a short term in-vitro culture. The findings indicate that in vitro proliferative capacity is maintained, at least under conditions of IL-2 supplementation, (which has been used for all HCV related studies thus far). Differences in T-cell function are unmasked under more rigorous conditions.

The results described herein indicate that HCV specific T cell responses are preserved at relatively high levels in the absence of detectable antigen. In contrast, responses in chronic infection are weaker and narrower, despite continuous antigenic stimulation, with little or no correlation between the HCV specific CD8+ T-cell response and viral load or disease activity. The HCV specific T cells in both resolved and chronic infection are similar in their functional and phenotypic properties. The early differentiated central memory phenotype seen in the presence of persistent viraemia is surprising.

Other embodiments are within the following claims.

What is claimed is:

1. An immunogenic composition comprising a purified Hepatitis C Virus (HCV) polypeptide, wherein said HCV polypeptide is HLA-Cw7 restricted and consists of the amino acid sequence of SEQ ID NO:52.

2. An immunogenic composition comprising a purified Hepatitis C Virus (HCV) polypeptide, wherein said HCV polypeptide is HLA-A29 restricted and consists of the amino acid sequence of SEQ ID NO:51.

* * * * *